(12) United States Patent
Lin et al.

(10) Patent No.: US 10,544,261 B2
(45) Date of Patent: Jan. 28, 2020

(54) PHOSPHINATED POLY(2,6-DIMETHYL PHENYLENE OXIDE) OLIGOMERS AND THERMOSETS THEREOF

(71) Applicant: Chang Chun Plastics Co., Ltd., Taipei (TW)

(72) Inventors: Ching Hsuan Lin, Taichung (TW); Ping-Chieh Wang, Taipei (TW); An-Pang Tu, Taipei (TW); Kuen-Yuan Hwang, Taipei (TW); Chun Yu Tseng, Taichung (TW)

(73) Assignee: Chang Chun Plastics Co., Ltd. (TW)

(*) Notice: Subject to any disclaimer, the term of this patent is extended or adjusted under 35 U.S.C. 154(b) by 0 days.

(21) Appl. No.: 15/287,962

(22) Filed: Oct. 7, 2016

(65) Prior Publication Data
US 2017/0101507 A1    Apr. 13, 2017

(30) Foreign Application Priority Data
Oct. 8, 2015  (TW) .............................. 104133283 A

(51) Int. Cl.
*C08G 65/40*  (2006.01)
*C07F 9/6574*  (2006.01)
(Continued)

(52) U.S. Cl.
CPC ...... *C08G 65/4006* (2013.01); *C07F 9/65744* (2013.01); *C08G 65/485* (2013.01);
(Continued)

(58) Field of Classification Search
CPC ........ C08G 79/04; C08K 3/36; C08K 5/5435; B32B 5/26; B32B 15/14; B32B 2260/023;
(Continued)

(56) References Cited

U.S. PATENT DOCUMENTS

| | | | |
|---|---|---|---|
| 4,837,276 A | 6/1989 | Fuhr et al. | |
| 6,995,195 B2 | 2/2006 | Ishii et al. | |

(Continued)

FOREIGN PATENT DOCUMENTS

| | | |
|---|---|---|
| CN | 101747378 A | 6/2010 |
| EP | 0275545 A1 | 7/1998 |

(Continued)

OTHER PUBLICATIONS

Hay, Allan S., "Polymerization by Oxidative Coupling: Discovery and Commercilization of PPO® and Noryl® Resins." Journal of Polymer Science: Part A: Polymer Chemistry, 1998, vol. 36, pp. 505-517.
(Continued)

*Primary Examiner* — Shane Fang
(74) *Attorney, Agent, or Firm* — Lerner, David, Littenberg, Krumholz & Mentlik, LLP

(57) ABSTRACT

The present invention relates to a phosphinated poly(2,6-dimethy phenylene oxide)oligomer, specifically an unsaturated group-containing phosphinated poly(2,6-dimethy phenylene oxide)oligomer, and processes for producing the same. A thermoset produced from the unsaturated group-containing phosphinated poly(2,6-dimethy phenylene oxide) oligomers according to the present invention exhibits flame retardancy and has a low dielectric constant and dissipation factor and a high glass transition temperature.

21 Claims, 6 Drawing Sheets

(51) Int. Cl.
*C08G 65/48* (2006.01)
*C08J 5/18* (2006.01)
*B29C 71/02* (2006.01)

(52) U.S. Cl.
CPC . *C08J 5/18* (2013.01); *C08J 7/08* (2013.01); *C08J 2371/12* (2013.01)

(58) Field of Classification Search
CPC ...... B32B 2260/046; B32B 2262/0269; B32B 2262/101; B32B 2307/204; B32B 2307/306; B32B 2307/3065; B32B 2457/08; H05K 1/0366
See application file for complete search history.

(56) References Cited

U.S. PATENT DOCUMENTS

| | | | |
|---|---|---|---|
| 2004/0077825 | A1 | 4/2004 | Hwang et al. |
| 2010/0004426 | A1 | 1/2010 | Lin et al. |
| 2010/0016585 | A1* | 1/2010 | Lin .................. C07F 9/657172 544/90 |
| 2010/0125154 | A1 | 5/2010 | Hsu et al. |
| 2014/0235886 | A1 | 8/2014 | Komiya et al. |

FOREIGN PATENT DOCUMENTS

| | | | |
|---|---|---|---|
| EP | 1384733 A1 | 1/2004 |
| JP | 2004059644 A | 2/2004 |
| JP | 2004067727 A | 3/2004 |
| JP | 2004143166 A | 5/2004 |
| JP | 2010059145 A | 3/2010 |
| JP | 2010116398 A | 5/2010 |
| JP | 2012052009 A | 3/2012 |
| JP | 2014156426 A | 8/2014 |
| JP | 2015067700 A | 4/2015 |

OTHER PUBLICATIONS

Fukuhara, Toshiaki, et al., "Synthesis of thermosetting poly(phenylene ether) containing allyl groups." Polymer, vol. 45, 2004, pp. 843-847.
Peters, Edward N., et al., "Polyphenylene Ether Macromonomers. I. Property Enhancements in Thermoset Resins via Novel Telechelic Oligomers." ANTEC, 2007, pp. 2125-2128.
Peters, Edward N. "Polyphenylene Ether Macromonomer: X. Vinyl Teriminated Telechelic Macromers." ANTECH, Jan. 13, 2011, pp. 1-8.
Lin, C.H., et al., "Catalyst-free synthesis of phosphinated poly(2,6-dimethyl-1,4-phenylene oxide) with high-Tg and low-dielectric charactheristic." Polymer Degradation and Stability, vol. 99, 2014, pp. 105-110.
Leu, Tsu-Shang, et al., "Synergistic Effect of a Phosphorous-Nitrogen Flame Retardant on Engineering Plastics." Journal of Applied Polymer Science, vol. 92, 2004, pp. 410-417.
Takeda, Kunihiko, et al., "Flame Retardancy and Rearrangement Reaction of Polyphenylene-ether/Polystyrene Alloy." Journal of Applied Science, 1997, vol. 64, pp. 1175-1183.
Chinese Search Report for CN Application No. 201510644048.0, dated Mar. 21, 2018.
Lin et al., "Catalyst-free Synthesis of Phosphinated Poly (2.6-Dimethyl-1.4-Phenylene Oxide) with High-Tg and Low-Dielctric Characteristic", Polymer Degradation and Stability 99, Jan. 2014, pp. 105-110.

* cited by examiner

PHOSPHINATED POLY(2,6-DIMETHYL PHENYLENE OXIDE) OLIGOMERS AND THERMOSETS THEREOF

FIELD OF THE INVENTION

The present invention relates to phosphinated poly(2,6-dimethyl phenylene oxide)oligomers and methods for producing the same. The unsaturated group-containing phosphinated poly(2,6-dimethyl phenylene oxide)oligomer according to the present invention can be cured to produce a flame resistant thermoset, which possesses flame retardancy and exhibits low dielectric constant, low dissipation factor, and high glass transition temperature (high-Tg).

BACKGROUND OF THE INVENTION

Semiconductor technology has developed over time to the point where device size is measured in micrometers. Consequently, a single layer of conductive wires may be insufficient to meet the specific demands of miniaturization. In this context, three-dimensional multilayer metal interconnections have been developed to fulfill the demands presented by ever-smaller devices. In multilayer metal interconnection fabrication technology, the properties of the metal interconnections would be influenced by two major factors: (1) RC delay caused by an electrically conductive metal wire and a dielectric layer, and (2) cross talk between electrically conductive metal wires. Furthermore, it is well known that signal transmission speed is inversely proportional to the square of a dielectric constant and is proportional to a dissipation factor. Given the above, developing a material having a low dielectric constant is an important issue nowadays.

Poly(2,6-dimethyl-1,4-phenylene oxide) (hereinafter referred to as PPO) developed by A. S. Hay of U.S. General Electric in 1956 pertains to an engineering plastic and a thermoplastic polymer [1]. PPO has a rigid chemical structure and thus is characterized by its high-Tg (about 210° C.), high tensile strength, rigidity, impact strength, and creep resistance and low coefficient of expansion (CTE: $2.9 \times 10^{-5}$ in/° F., $-20°$ F. to $150°$ F.). In addition, PPO advantageously has good solvent resistance, acid resistance, alkali resistance and low water absorption rate. Since a polymer product is often formed by an injection molding technique, PPO also possesses advantageously low molding shrinkage. Regarding electronic properties, PPO has a low dielectric constant. To fulfill the demands of high performance and dimensional stability, the resin for a copper foil substrate is required to be thermoset. However, due to the limitation of the inherent chemical structure of PPO, PPO is difficult to cure through self-crosslinking. Therefore, developments and applications of PPO substrates have been limited. Ueda et al. conducted an oxidative coupling reaction to copolymerize 2,6-dimethylphenol and 2-allyl-6-methylphenol such that a PPO having pendant allyl group is produced [2]. The modified PPO becomes a self-curable thermoset polymer. The cured modified PPO still possesses high Tg and low dielectric constant. However, because PPO has a high molecular weight, PPO exhibits relatively high viscosity and poor solubility and impregnation to glass fiber. Therefore, the applications of PPO in the copper foil substrate are limited.

In 2006, Ishii et al. synthesized a telechelic PPE macromonomer (PPE-M) having low molecular weight. The end-capping phenolic group of the macromonomer is reacted with 4-chloromethylstyrene to produce a PPO compound having a vinylbenzene end-capping group. The chemical structure of the resulting vinylbenzyl PPE macromonomer (VB-PPE-M) is shown in Scheme (1) below [3]. In 2007, Peters et al. copolymerized PPE-M, an epoxy resin, and cyanate to improve the properties of a thermoset [4]. In 2011, Peters et al. modified the phenolic end-capping group of PPE-M (or Noryl® SA-90) from SABIC such that an double bond is introduced to the end-capping group of PPE-M [5]. As shown in Scheme 1, when a methacrylate end-capping group is attached to PPE-M, a methacrylated PPE macromonomer (M-PPO-M) shown in Scheme (1) is produced, which has product name NORYL™ Resin SA 9000.

Scheme 1: PPO having unsaturated group

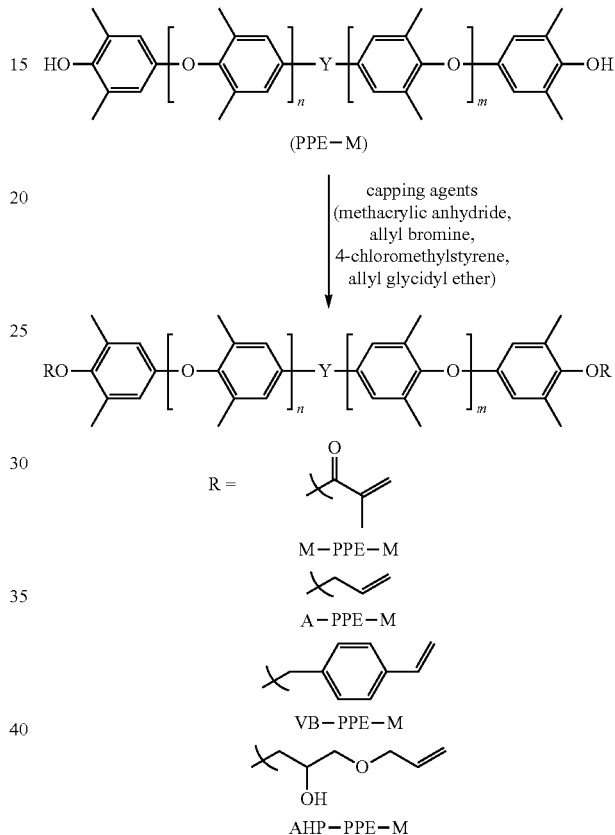

High frequency printed circuit boards have strict requirements in terms of electrical and thermal properties and flame retardance. In particular, such circuit boards need to achieve grade V-0 on a flammability test. Therefore, the PPO material in this regard should be improved so as to fulfill market demands and increase its value. However, PPO is flammable and cannot achieve the UL-94 grade V-0 requirement for an electronic device. Recent research shows that an organophosphorus compound can impart a desired flame retardancy to a polymer. In addition, in comparison with a halogen-based flame retardant, an organophosphorus compound pertains to a solid phase flame retardant, which generates less smoke and toxic gases. In contrast, a conventional additive flame retardant not only degrades the material mechanical properties but also reduces flame retardancy due to the migration or volatilization of the flame retardant molecules. Early studies show that adding a flame retardant can achieve advantageous flame retardancy. For instance, Leu et al. demonstrated adding phosphinated nitrogen-containing flame retardant to PPO [6]. Due to the synergistic effect of nitrogen and phosphorus comprised in a flame retardant, the UL-94 flammability reached grade V-0. In addition, in a PPO and polystyrene (PS) mixture system, although the impact strength of PPO is improved, its flame retardancy is still degraded. Therefore, an additional flame retardant should be added to achieve a desired flame retardancy. In this connection, Takeda et al. studied the flame retardancy of PPO/PS by using different phosphorus-containing aromatic retardants [7]. They found that adding a phosphorus-containing flame retardant can effectively reduce the self-extinguishing time of burning. Therefore, the flame retardancy can be improved. Furthermore, in 2014, Lin et al. discloses a series of phosphinate-derivatives, e.g., 9,10-dihydro-9-oxa-10-phosphaphenanthrene-10-oxide (hereunder referred to as DOPO). They directly introduced a flame-retardant phosphorus-containing group to the PPO structure so as to replace the additionally added flame retardant [8]. Their results reveal that the UL-94 flammability reaches grade VTM-0 when the phosphorus content is 1% and prove that introducing a phosphorus-containing group to PPO can effectively improve flame retardancy.

REFERENCES

1. Hay, A. S., J. Polym Sci Part A: Polym Chem, 1998, 36, 505.
2. Fukuhara, T.; Shibasaki, Y.; Ando, S.; Ueda, M., Polymer 2004, 45, 843.
3. U.S. Pat. No. 6,995,195 B2
4. E. N. Peters, A. K., E. Delsman, H. Guo, A. Carrillo, G. Rocha, in Society of Plastics Engineers Annual Technical Conference (ANTEC 2007): Plastics Encounter, Cincinnati, Ohio, 6-11 May 2007; Curran Associates, Inc.; pp 2125-2128.
5. S. Fisher, H. G., M. Jeevanath, E. Peters, SABIC Innovative Plastics, in *Polyphenylene Ether Macromonomer: X. Vinyl Terminated Telechelic Macromers*, 69th Annual Technical Conference of the Society of Plastics Engineers 2011 (ANTEC 2011), Boston, Mass., USA, 1-5 May 2011; pp 2819-2822.
6. Leu, T. S.; Wang, C. S., J Appl Polym Sci, 2004, 92, 410.
7. Kunihiko, T.; Fumiko, A.; Masao, K.; Shigeki, T., J Appl Polym Sci, 1997, 64, 1175.
8. Lin, C. H., Tsai, Y. J., Shih, Y. S., Chang, H. C., Polym Degradation and Stability, 2014, 99, 105.

SUMMARY OF THE INVENTION

The present invention pertains to phosphinated poly(2,6-dimethyl phenylene oxide)oligomers. Specifically, the present invention includes two embodiments. Firstly, a phosphorus group is introduced to PPO to produce a bisphenol oligomer having a phosphorous group, particularly a phosphinated poly(2,6-dimethyl phenylene oxide)bisphenol oligomer. Secondly, the produced phosphinated poly(2,6-dimethyl phenylene oxide)bisphenol oligomer is modified. Three different unsaturated groups—are introduced to the oligomer to produce an unsaturated group-containing phosphinated poly(2,6-dimethyl phenylene oxide)oligomer. For example, a phosphinated poly(2,6-dimethyl phenylene oxide)bisphenol oligomer is reacted with 4-chloromethylstyrene to produce styrenated and phosphinated PPO. Since a styrene group has low polarity and is hydrophobic, this would result in a low dielectric constant and dissipation factor. Therefore, a thermoset exhibiting flame retardancy and having a low dielectric constant can be obtained.

DETAILED DESCRIPTION OF THE INVENTION

Phosphinated poly(2,6-dimethyl phenylene oxide)oligomers

Figure 1:
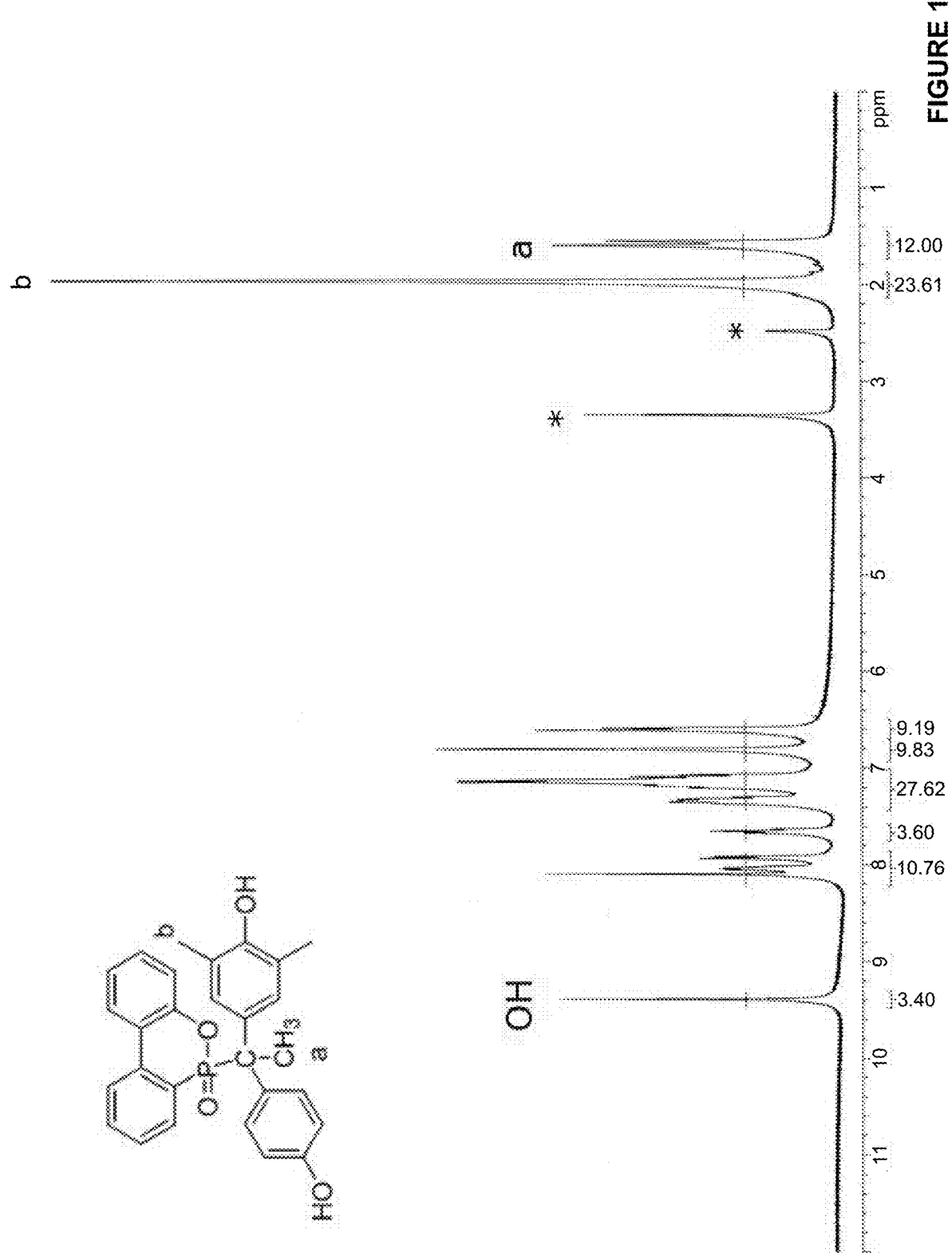
FIG. 1 shows a $^1$H-NMR spectrum of synthesized phosphinated methylphenol.

The phosphinated poly(2,6-dimethyl phenylene oxide) oligomer according to the present invention comprises a structure of formula (2):

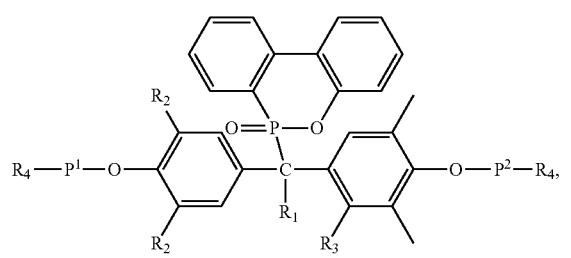

(2)

wherein each group has the following meaning:
$P^1$ denotes

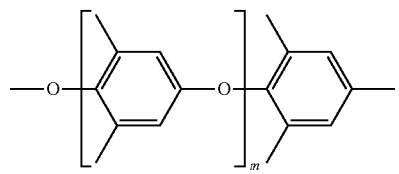

or does not exist;
$P^2$ denotes

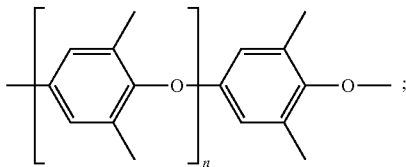

$R_1$, $R_2$, $R_3$ each independently denotes H or straight chain or branched chain alkyl having 1 to 6 C-atoms, preferably H, methyl, or ethyl;
$R_4$ denotes H, alkenyl or aryl having 1 to 10 C-atoms and comprising 0 to 3 oxygen atoms, or the combination thereof, preferably

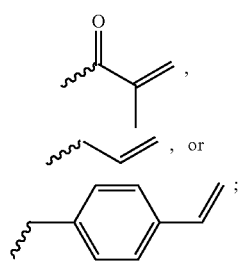

m, n each independently denotes an integer from 0 to 30, preferably an integer from 0 to 20.

Phosphinated poly(2,6-dimethyl Phenylene Oxide) Bisphenol Oligomers

In a phosphinated poly(2,6-dimethyl phenylene oxide) oligomer of the present invention, when $R^4$ is H, the oligomer of formula (2) is a phosphinated poly(2,6-dimethyl phenylene oxide)bisphenol oligomer. In addition, at least an oligomer of formula (2) is represented by formula (3):

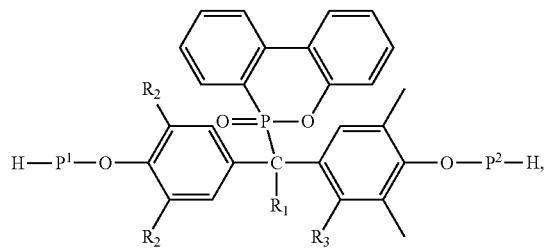
(3)

wherein each group has the following meaning:

$P^1$ denotes

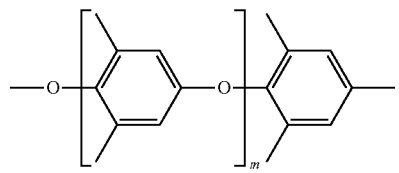

or does not exist;

$P^2$ denotes

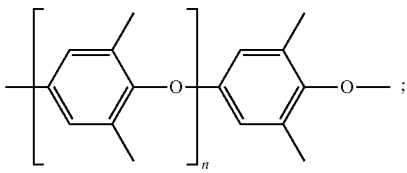

$R_1, R_2, R_3$ each independently denotes H, or straight chain or branched chain alkyl having 1 to 6 C-atoms, preferably H, methyl, or ethyl;

m, n each independently denotes an integer from 0 to 30, preferably an integer from 0 to 20.

In an embodiment of the present invention, at least an oligomer of formula (3) is represented by formula (IIa) or formula (IIc):

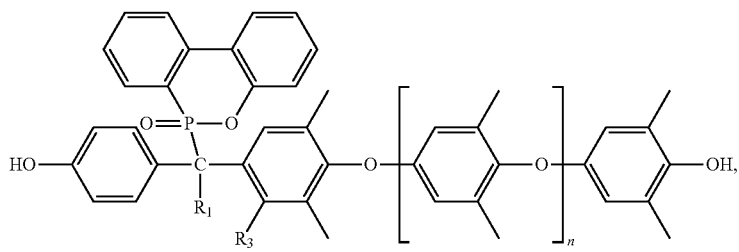
(IIa)

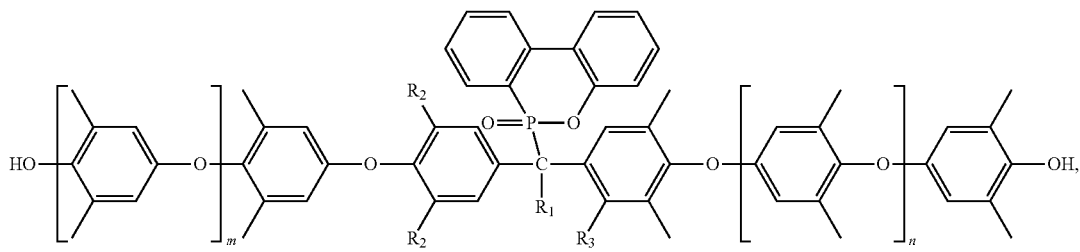
(IIc)

wherein each group has the following meaning:
R₁, R₂, R₃ each independently denotes H or straight chain or branched chain alkyl having 1 to 6 C-atoms, preferably H, methyl, or ethyl;
m, n each independently denotes an integer from 0 to 30, preferably an integer from 0 to 20.

In an embodiment of the present invention, formula (IIa) preferably is:

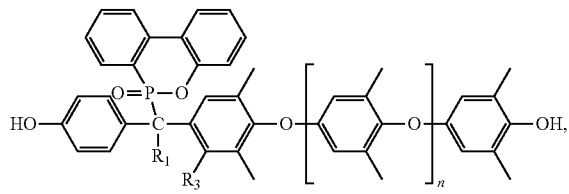

(IIa)

wherein R₁ is H, CH₃, or C₂H₅, and R₃ is H or CH₃.

In an embodiment of the present invention, formula (IIc) preferably is:

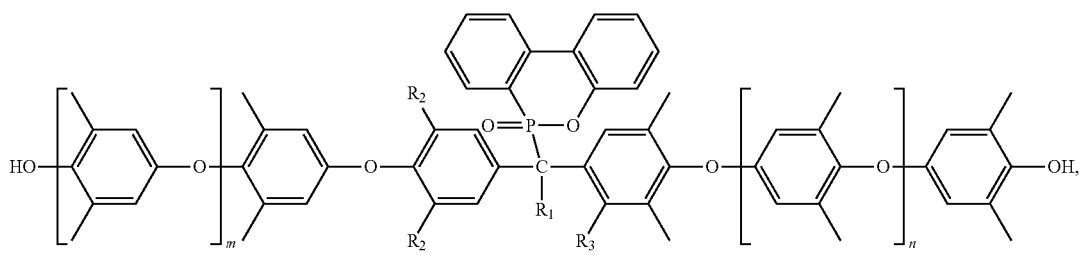

(IIc)

wherein R₁ is H, CH₃, or C₂H₅, R₂ is H or CH₃, and R₃ is H or CH₃; or

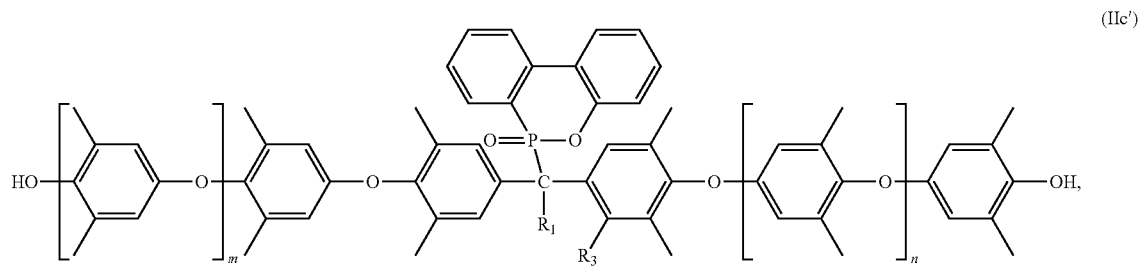

(IIc')

wherein R₁ is H, CH₃, or C₂H₅, and R₃ is H or CH₃.

Unsaturated Group-Containing Phosphinated Poly(2,6-dimethyl Phenylene Oxide) Oligomers In a phosphinated poly(2,6-dimethyl phenylene oxide) oligomer according to the present invention, when R⁴ is not H, the oligomer of formula (2) is directed to an unsaturated group-containing phosphinated poly(2,6-dimethyl phenylene oxide)oligomer, wherein at least an oligomer of formula (2) is represented by formula (4):

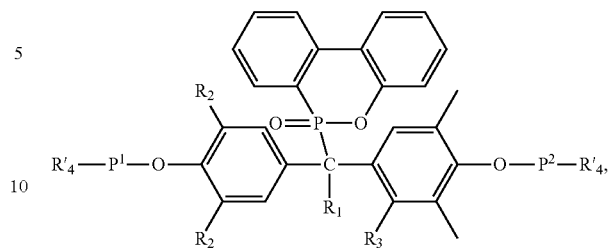

(4)

wherein each group has the following meaning:
P¹ denotes

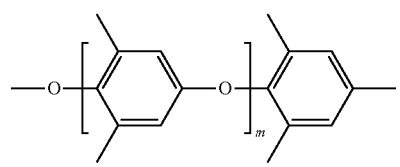

or does not exist;

P² denotes

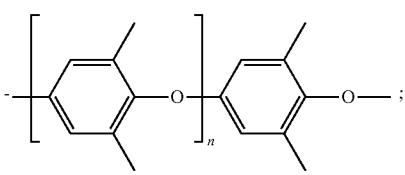

R₁, R₂, R₃ each independently denotes H or straight chain or branched chain alkyl having 1 to 6 C-atoms, preferably H, methyl, or ethyl;

R'$_4$ denotes H, alkenyl or aryl having 1 to 10 C-atoms and comprising 0 to 3 oxygen atoms, or the combination thereof, preferably

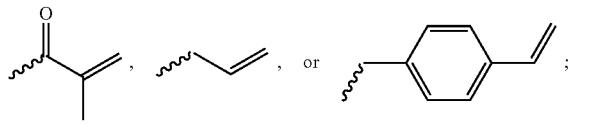

m, n each independently denotes an integer from 0 to 30, preferably an integer from 0 to 20.

In an embodiment of the present invention, at least an oligomer of formula (4) is represented by formula (IIIa) or (IIIc):

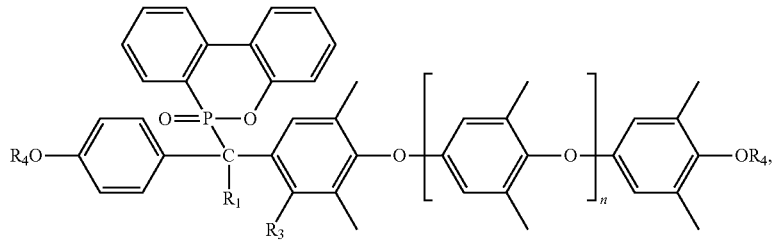

(IIIa)

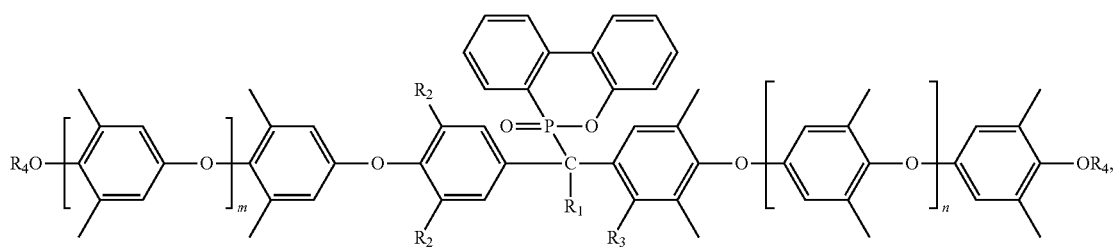

(IIIc)

wherein each group has the following meaning:
- R$_1$, R$_2$, R$_3$ each independently denotes H or straight chain or branched chain alkyl having 1 to 6 C-atoms, preferably H, methyl, or ethyl;
- R$_4$ denotes H, alkenyl or aryl having 1 to 10 C-atoms and comprising 0 to 3 oxygen atoms, or the combination thereof, preferably is

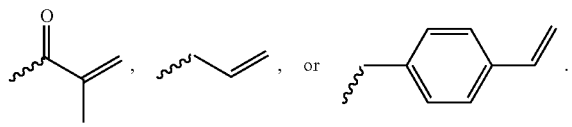

m, n each independently denotes an integer from 0 to 30, preferably an integer from 0 to 20.

In an embodiment of the present invention, formula (IIIa) preferably is:

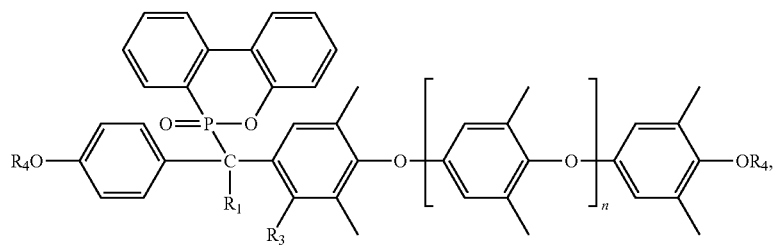

(IIIa)

wherein $R_1$ is H, $CH_3$, or $C_2H_5$, $R_3$ is H or $CH_3$, and $R_4$ is

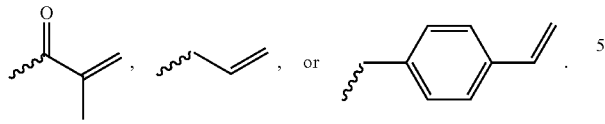

In an embodiment of the present invention, formula (IIIc) preferably is:

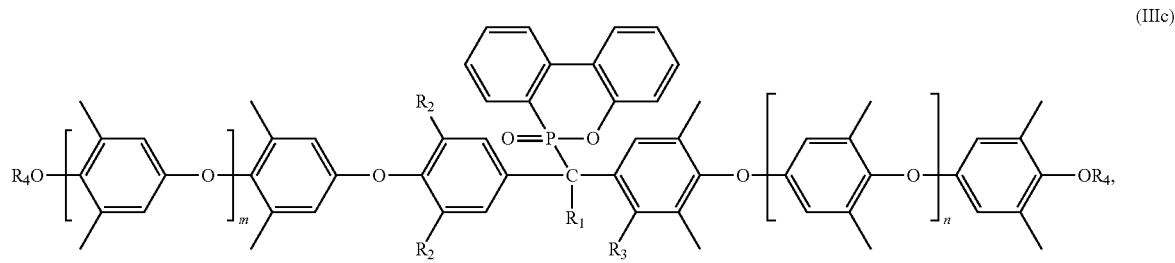

(IIIc)

wherein $R_1$ is H, $CH_3$, or $C_2H_5$, $R_2$ is H or $CH_3$, $R_3$ is H or $CH_3$, and $R_4$ is

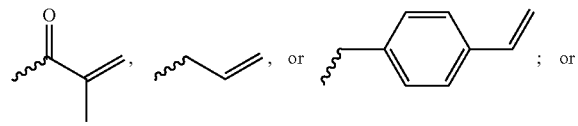

; or

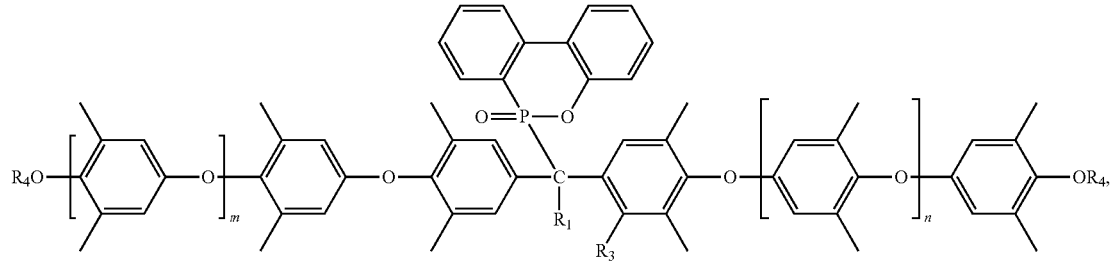

(IIIc')

wherein $R_1$ is H, $CH_3$, or $C_2H_5$, $R_3$ is H or $CH_3$, and $R_4$ is

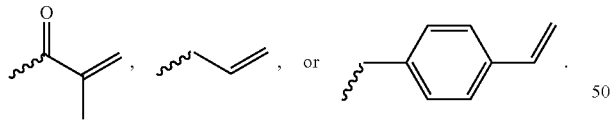

In an embodiment of the present invention, the oligomer of formula (4) comprises an unsaturated group-containing phosphinated poly(2,6-dimethyl phenylene oxide) oligomer of formula (IIIc-M), (IIIc-A), or (IIIc-VB).

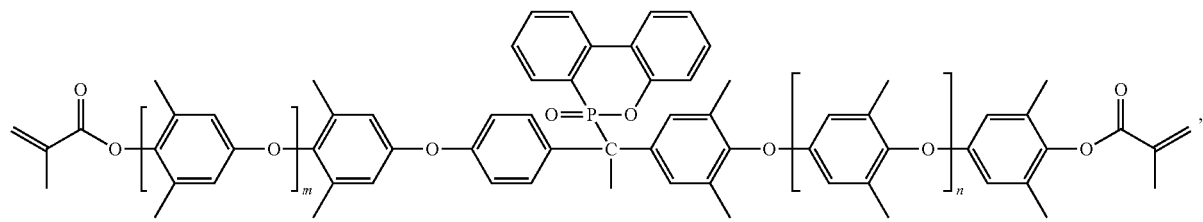

(IIIc-M)

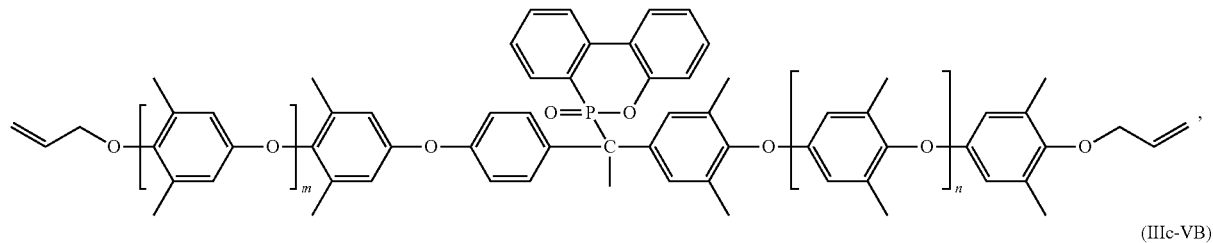

(IIIc-A)

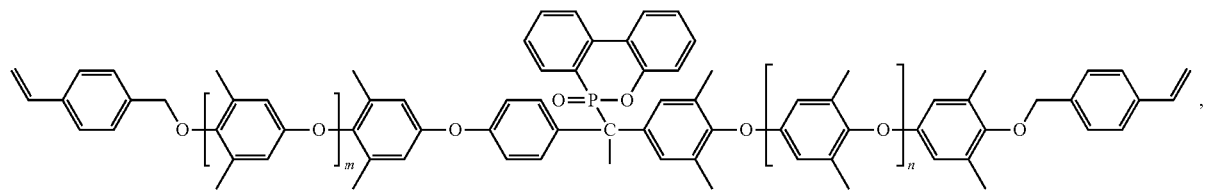

(IIIc-VB)

wherein m or n each independently denotes an integer from 0 to 30, preferably an integer from 0 to 20.

Process for Producing a Phosphinated Poly(2,6-dimethyl phenylene oxide)bisphenol oligomer In the process for producing an oligomer according to the invention, the phosphinated bisphenol compound of formula (I) is first synthesized by way of the following scheme:

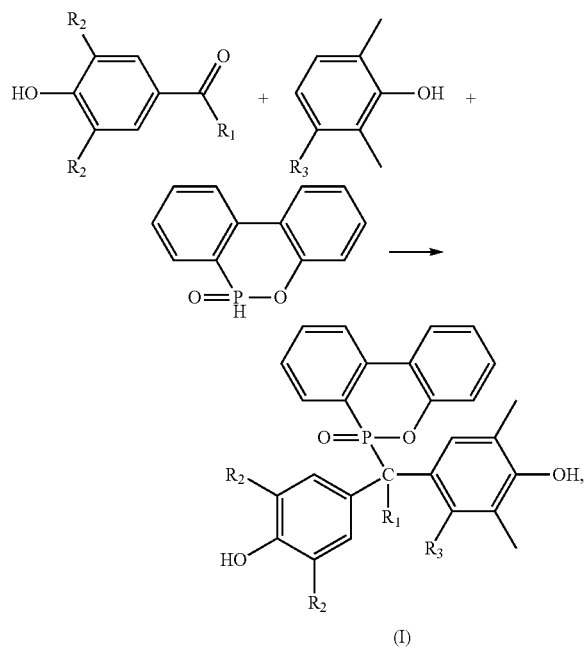

(I)

wherein $R_1$, $R_2$ or $R_3$ each independently denotes H or straight chain or branched chain alkyl having 1 to 6 C-atoms, preferably H, methyl, or ethyl. Then, the bisphenol compound of formula (I) is reacted with 2,6-dimethylphenol under the catalysis of CuCl and an amine compound, such as dibutylamine (DBA) or 4-dimethylaminopyridine (DMAP), to produce a phosphinated poly(2,6-dimethyl phenylene oxide)bisphenol oligomer.

In an embodiment of the present invention, the process for producing a phosphinated poly(2,6-dimethyl phenylene oxide)bisphenol oligomer of formula (2) includes reacting the compound of formula (I) with 2,6-dimethylphenol under the catalysis of CuCl and an amine compound, such as dibutylamine or 4-dimethylaminopyridine, to produce a phosphinated poly(2,6-dimethyl phenylene oxide)bisphenol oligomer, wherein $R_1$ or $R_2$ each independently denotes H or straight chain or branched chain alkyl having 1 to 6 C-atoms, preferably H, methyl, or ethyl.

In the process for producing an oligomer according to the present invention, the produced phosphinated poly(2,6-dimethyl phenylene oxide)bisphenol oligomer comprises at least an oligomer of formula (3).

Specifically, in the process for producing an oligomer according to the present invention, the produced phosphinated poly(2,6-dimethyl phenylene oxide)bisphenol oligomer comprises at least an oligomer of formula (IIa) or (IIc').

In the process for producing an oligomer according to the present invention, when $R_2$ is H, the produced phosphinated poly(2,6-dimethyl phenylene oxide)bisphenol oligomer comprises an oligomer of formula (IIa):

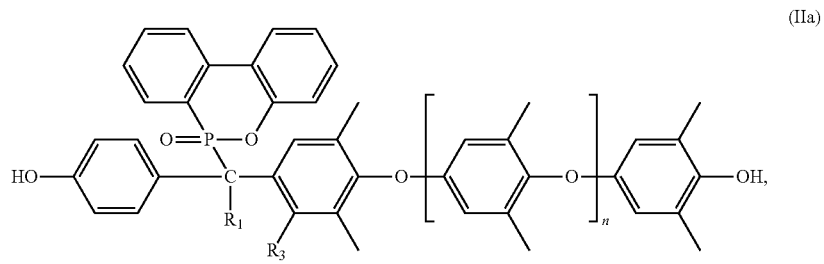

(IIa)

wherein $R_1$ is H, $CH_3$, or $C_2H_5$, and $R_3$ is H or $CH_3$.

In the process for producing an oligomer according to the present invention, when $R_2$ is $CH_3$, the produced phosphinated poly(2,6-dimethyl phenylene oxide)bisphenol oligomer comprises an oligomer of formula (IIc'):

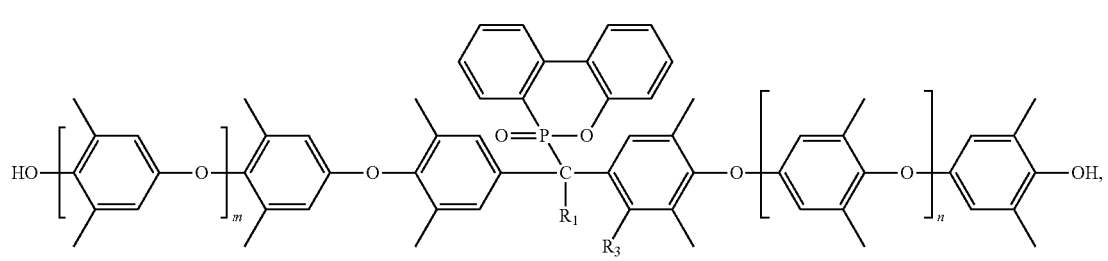

(IIc')

wherein $R_1$ is H, $CH_3$, or $C_2H_5$, and $R_3$ is H or $CH_3$.

One method for producing bisphenol group-containing PPO is by way of a redistribution reaction associated with bisphenol and high molecular weight PPO. However, the redistribution reaction usually produces a product having bimodal molecular weight distribution due to the occurrence of a side reaction. Because of the poor solubility and impregnation of the high molecular weight product, the application in a copper foil substrate is thus restricted. Quite different from the conventional technique, the present invention utilizes a PPO oligomer, such as SABIC SA-90, as a starting material to conduct a redistribution reaction for phosphinated diphenol and SA-90 to produce a phosphinated poly(2,6-dimethyl phenylene oxide)bisphenol oligomer that exhibits improved solubility and impregnation to glass fiber and exhibits flame retardancy.

According to an embodiment of the present invention, the process for producing an oligomer includes conducting a redistribution reaction for the compound of formula (I) and a poly(2,6-dimethyl phenylene oxide)oligomer of formula (5):

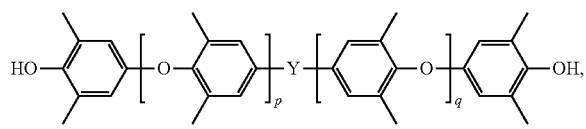

(5)

under the catalysis of a benzoyl peroxide to produce a phosphinated poly(2,6-dimethyl phenylene oxide)bisphenol oligomer, wherein Y denotes

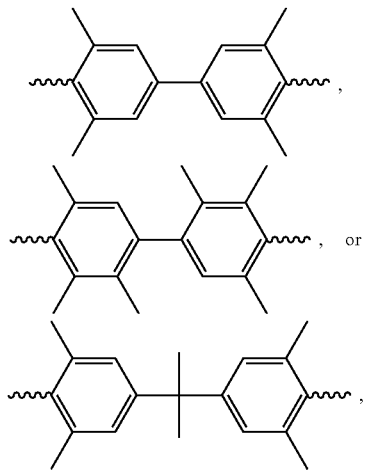

and p, q each independently denotes an integer from 0 to 50.

According to an embodiment of the present invention, the produced phosphinated poly(2,6-dimethyl phenylene oxide) bisphenol oligomer comprises at least an oligomer of formula (3).

Specifically, in the process for producing an oligomer according to the invention, the produced phosphinated poly (2,6-dimethyl phenylene oxide)bisphenol oligomer comprises at least an oligomer of formula (IIc).

In the process for producing an oligomer according to the invention, the produced phosphinated poly(2,6-dimethyl phenylene oxide)bisphenol oligomer comprises an oligomer of formula (IIc):

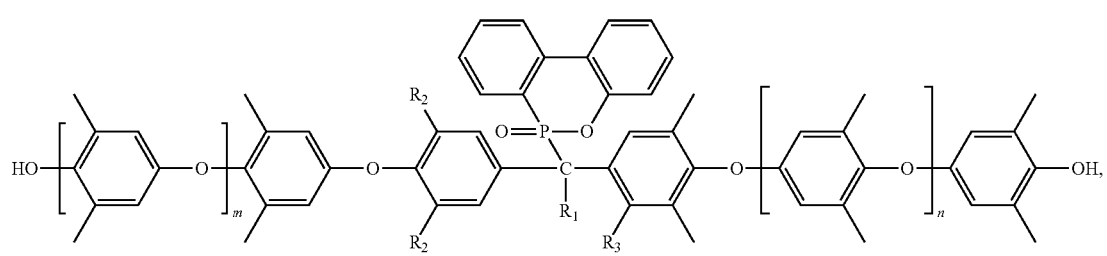

(IIc)

wherein $R_1$ is H, $CH_3$, or $C_2H_5$, $R_2$ is H or $CH_3$, and $R_3$ is H or $CH_3$.

Process for Producing an Unsaturated Group-Containing Phosphinated Poly(2,6-dimethyl Phenylene Oxide) Oligomer The process for producing an unsaturated group-containing phosphinated poly(2,6-dimethyl phenylene oxide)oligomer includes reacting the end-capping hydroxyl group of the produced phosphinated poly(2,6-dimethyl phenylene oxide)bisphenol oligomer with methacrylic anhydride, allyl bromine, or 4-chloromethylstyrene under the catalysis of a alkali catalyst to produce an unsaturated group-containing phosphinated poly(2,6-dimethyl phenylene oxide)oligomer.

According to an embodiment of the present invention, the produced unsaturated group-containing phosphinated poly(2,6-dimethyl phenylene oxide)oligomer comprises at least an oligomer of formula (4).

Specifically, according to an embodiment of the present invention, the produced unsaturated group-containing phosphinated poly(2,6-dimethyl phenylene oxide) oligomer comprises at least an oligomer of formula (IIIa) or (IIIc):

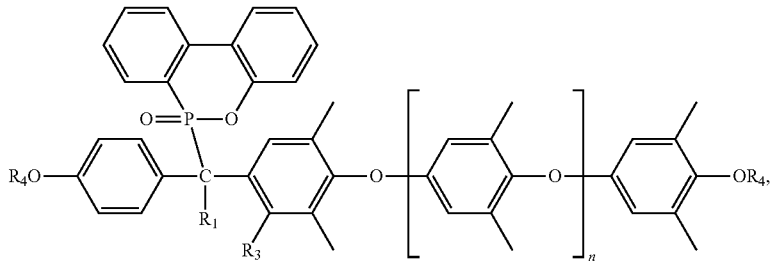

(IIIa)

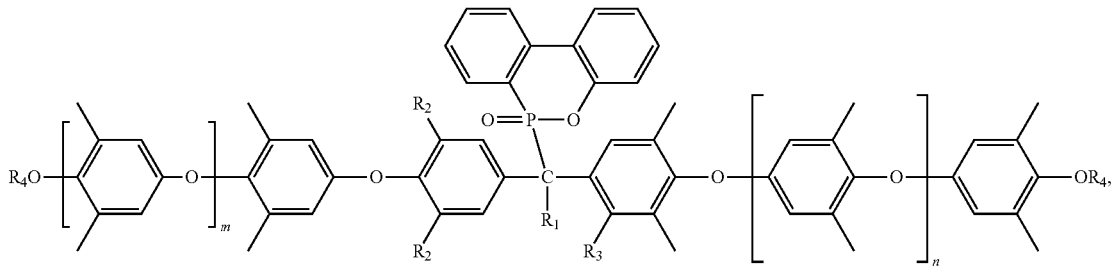

(IIIc)

wherein $R_1$, $R_2$ or $R_3$ each independently denotes H or straight chain or branched chain alkyl having 1 to 6 C-atoms, preferably H, methyl or ethyl, and $R_4$ denotes H, alkenyl or aryl having 1 to 10 C-atoms and comprising 0 to 3 oxygen atoms, or the combination thereof, preferably

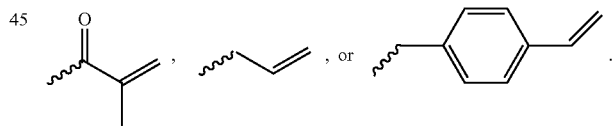

Specifically, according to an embodiment of the present invention, the produced unsaturated group-containing phosphinated poly(2,6-dimethyl phenylene oxide) oligomer comprises at least an oligomer of formula (IIIa):

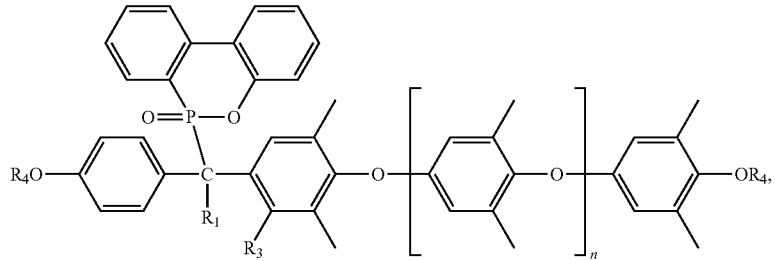

(IIIa)

wherein $R_1$ is H, $CH_3$, or $C_2H_5$, $R_3$ is H or $CH_3$, and $R_4$ is

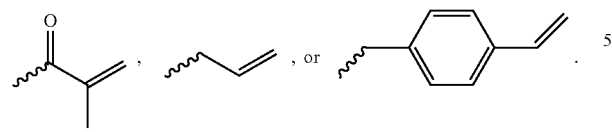

According to an embodiment of the present invention, the produced unsaturated group-containing phosphinated poly (2,6-dimethyl phenylene oxide)oligomer comprises an oligomer of formula (IIIc) or (IIIc'):

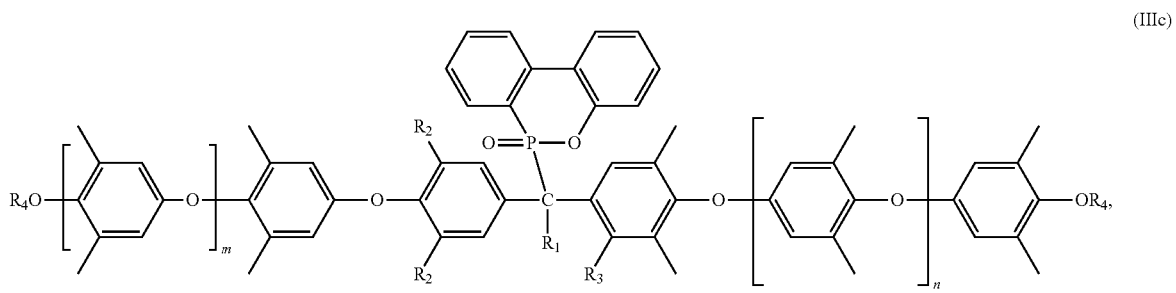

(IIIc)

wherein $R_1$ is H, $CH_3$, or $C_2H_5$, $R_2$ is H or $CH_3$, $R_3$ is H or $CH_3$, and $R_4$ is

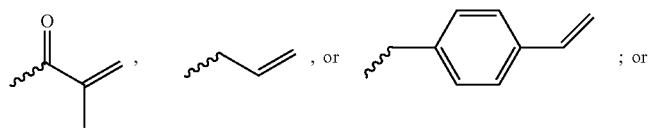

; or

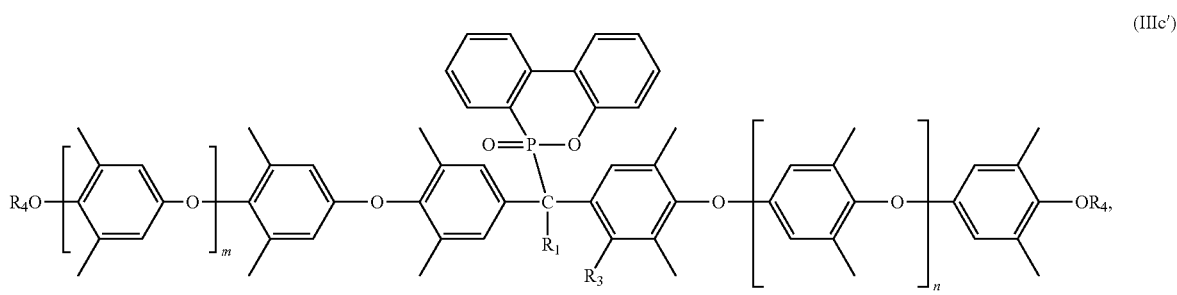

(IIIc')

wherein $R_1$ is H, $CH_3$, or $C_2H_5$, $R_3$ is H or $CH_3$, and $R_4$ is

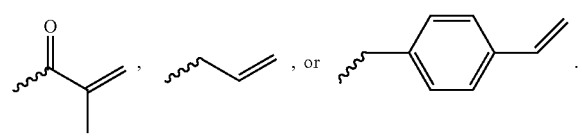

In the process for producing an oligomer according to the present invention, the alkali catalyst is selected from the group consisting of potassium carbonate ($K_2CO_3$), sodium carbonate ($Na_2CO_3$), potassium hydroxide (KOH), sodium hydroxide (NaOH), sodium bicarbonate ($NaHCO_3$), or the combination thereof.

In the process for producing an oligomer according to the present invention, the produced unsaturated group-containing phosphinated poly(2,6-dimethyl phenylene oxide) oligomer is represented by formula (IIIc-M):

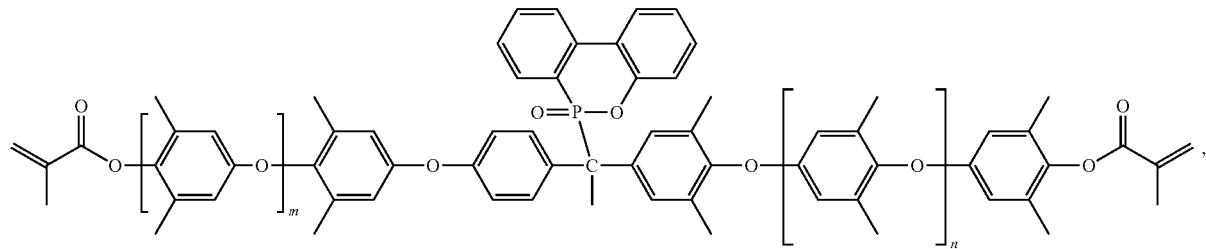

(IIIc-M)

wherein m or n each independently denotes an integer from 0 to 30, preferably an integer from 0 to 20.

In the process for producing an oligomer according to the present invention, the produced unsaturated group-containing phosphinated poly(2,6-dimethyl phenylene oxide) oligomer is represented by formula (IIIc-A):

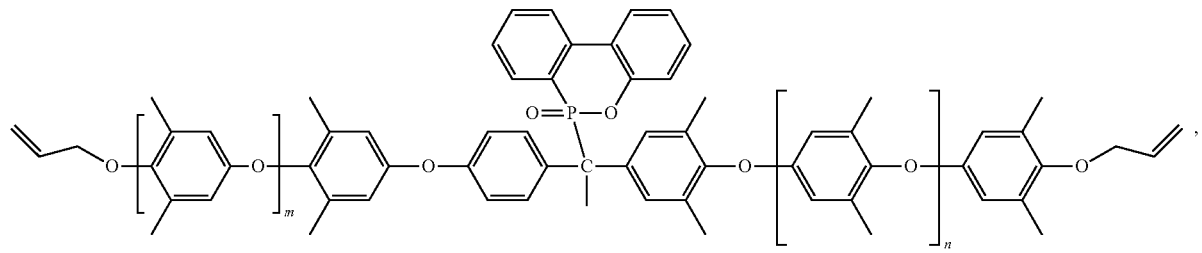

(IIIc-A)

wherein m or n each independently denotes an integer from 0 to 30, preferably an integer from 0 to 20.

In the process for producing an oligomer according to the present invention, the produced unsaturated group-containing phosphinated poly(2,6-dimethyl phenylene oxide) oligomer is represented by formula (IIIc-VB):

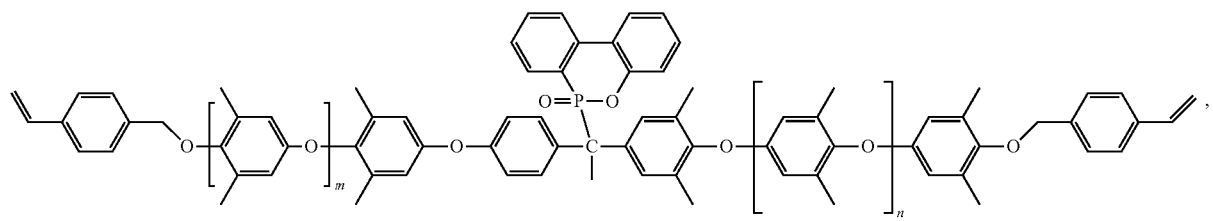

(IIIc-VB)

wherein m or n each independently denotes an integer from 0 to 30, preferably an integer from 0 to 20.

Thermoset Produced from an Unsaturated Group-Containing Phosphinated Poly(2,6-Dimethyl Phenylene Oxide) Oligomer and the Process for Producing the Same An unsaturated group-containing phosphinated poly(2,6-dimethyl phenylene oxide)oligomer of formula (4) is subjected to an unsaturated group reaction by using a peroxide as a radical initiator to produce a thermoset that exhibits flame retardancy and has a low dielectric constant and dissipation factor and a high-Tg.

In the process for producing a thermoset according to the invention, an oligomer of formula (4) is cured by using a radical initiator to produce a thermoset that exhibits flame retardancy and has a low dielectric constant and dissipation factor and a high-Tg.

In the process for producing a thermoset according to the invention, the radical initiator comprises a peroxide, preferably t-butyl cumyl peroxide (TBCP).

In the process for producing a thermoset according to the invention, an unsaturated group-containing phosphinated poly(2,6-dimethyl phenylene oxide)oligomer of formula (IIIc-M) is cured by using a radical initiator, such as t-butyl cumyl peroxide (TBCP), to produce a thermoset that exhibits flame retardancy and has a low dielectric constant and dissipation factor and a high-Tg.

In the process for producing a thermoset according to the invention, an unsaturated group-containing phosphinated poly(2,6-dimethyl phenylene oxide)oligomer of formula (IIIc-A) is cured by using a radical initiator, such as t-butyl cumyl peroxide (TBCP), to produce a thermoset that exhibits flame retardancy and has a low dielectric constant and dissipation factor and a high-Tg.

In the process for producing a thermoset according to the invention, an unsaturated group-containing phosphinated poly(2,6-dimethyl phenylene oxide)oligomer of formula (IIIc-VB) is cured by using a radical initiator, such as t-butyl cumyl peroxide (TBCP), to produce a thermoset that exhibits flame retardancy and has a low dielectric constant and dissipation factor and a high-Tg.

EXAMPLE

The inventions are demonstrated and illustrated in the following working examples.

While the following description contains many specifics, these specifics should not be construed as limitations to the scope of the inventions, but merely as exemplifications of preferred embodiments thereof. Those skilled in the art will envision many other possible variations that are within the scope and spirit of the inventions as defined by the claims appended hereto.

Example 1

Synthesis of Phosphinated Methylphenol 10.0 g (73.4 mmol) p-hydroxyacetophenone, 15.9 g (73.4 mmol) 9,10-dihydro-9-oxa-10-phosphaphenanthrene-10-oxide, 44.40 g (73.4×5 mmol) 2,6-dimethylphenol, and 0.64 g p-toluenesulfonic acid (i.e. 4 wt % of 9,10-dihydro-9-oxa-10-phosphaphenanthrene-10-oxide) were reacted under a nitrogen atmosphere at 130° C. for 24 hours. After the reaction was terminated, the product was filtered at an elevated temperature to obtain a filtered cake. The white powder was obtained by using methanol to rinse the filtered cake several times. After suction filtration, the white powder was dried in a vacuum oven at a temperature of 80° C. The yield was about 85%.

FIG. 1 shows a $^1$H NMR spectrum of monomer of the synthesized phosphinated methylphenol. It can be found that the characteristic peak of $CH_3$(a) is at 1.6 ppm, the characteristic peak of $CH_3$(b) is at 2.0 ppm, and the characteristic peak of Ar—OH is at 9.4 ppm. In addition, a peak at 38.0 ppm can be found in the $^{31}$P NMR spectrum. It was confirmed that the resulting structure is correct.

Example 2

Synthesis of Phosphinated Methyl Polyphenylene Oligomer of Formula (IIa)

Figure 2:
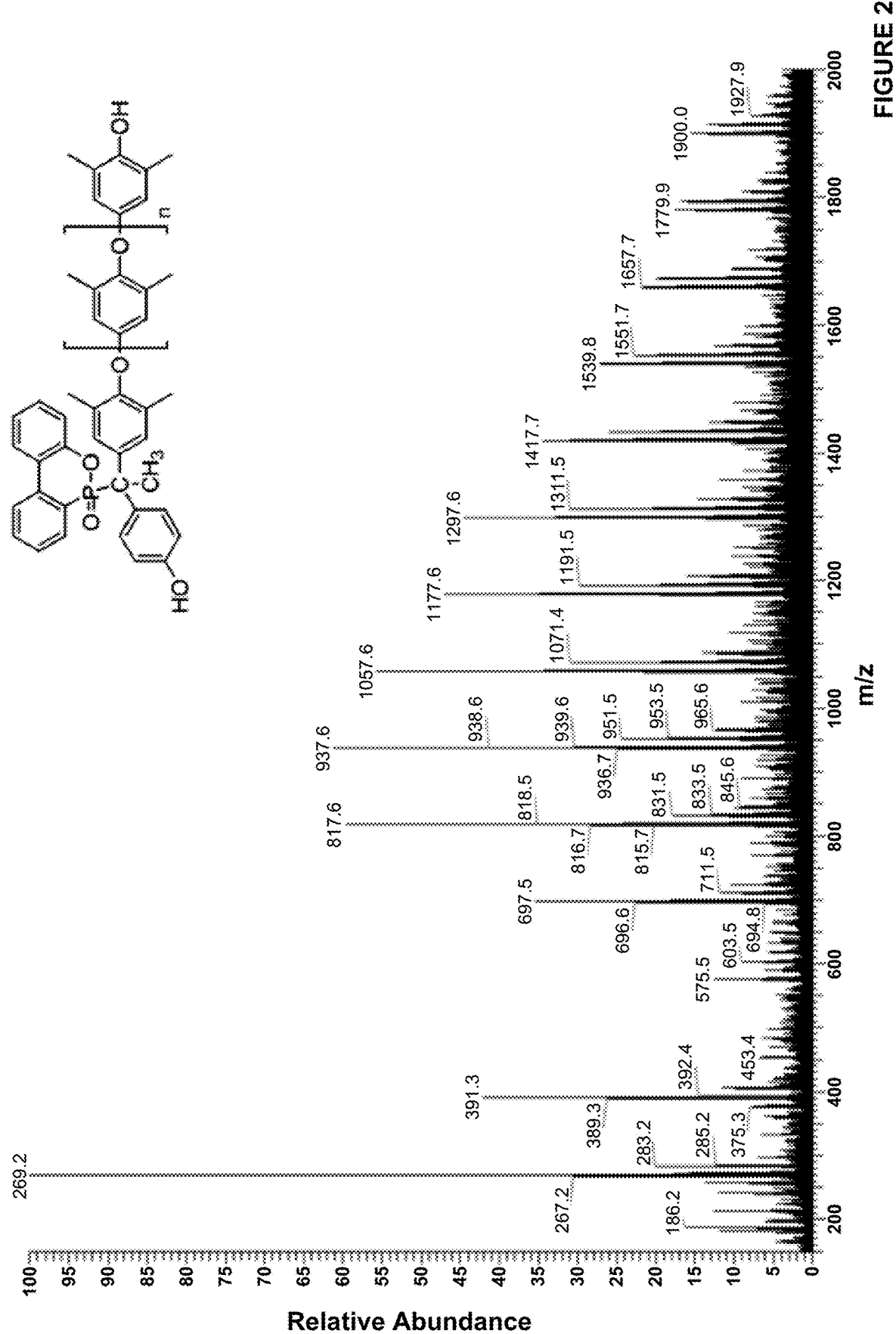
FIG. 2 shows an LC/MS spectrum of an oligomer of formula (IIa).

0.079 g (0.8 mmole) CuCl and 0.095 g (0.78 mmole) DMAP were dissolved in a 1-methyl-2-pyrrolidone (NMP) solvent of 25 mL. After injecting oxygen gas for 10 mins at room temperature, 0.739 g (1.62 mmole) of monomer (1) and 0.979 g (8.01 mmole) 2,6-dimethylphenol were added to the solution. Under an oxygen atmosphere, the reaction was conducted at a temperature of 40° C. for 4 hours. After the reaction was terminated, a filtrate was obtained through suction filtration. The product was precipitated by adding methanol to the filtrate and was then rinsed several times. After a second suction filtration, the filtered cake was dried in a vacuum oven at a temperature of 80° C. to produce a khaki product IIa. FIG. 2 shows an LC/MS spectrum of the product IIa. The peak of 697.5 m/z corresponds to the molecular weight of n=1. The molecular structure of n=2 to n=11 can also be found in FIG. 2.

Example 3

Synthesis of Phosphinated Methyl Polyphenylene Oxide of Formula (IIc)

4.0 g (8.76 mmol) phosphinated methylphenol produced in Example 1 and 4 g (8.76×3.8 mmol) SABIC SA-90, and 0.404 g (1/40 mol of SA-90) benzoyl peroxide were dissolved in an NMP solvent and reacted under a nitrogen atmosphere at a temperature of 130° C. for 12 hours. After the reaction was terminated, a brown powder was precipitated by using methanol/water and was then rinsed several times. After suction filtration, the filtered cake was dried in a vacuum oven at a temperature of 70° C. The yield was about 90%. The $^1$H NMR spectrum shows that the peak(s) around 6 to 8.5 ppm correspond(s) to the hydrogen signal originating from diphenyl of the biphenylene phosphinate structure. The GPC data (using tetrahydrofuran (THF) as an eluent and polystyrene as a standard) reveals that the number-average molecular weight and weight-average molecular weight of SA-90 are 1,508 and 3,978 g/mol, respectively. The number-average molecular weight and weight-average molecular weight of the oligomer of formula (IIIc) are 787 and 2,625 g/mole, respectively. The above results confirm that after conducting the redistribution reaction, the average molecular weight tends to be reduced, and this is advantageous for improving the solubility and impregnation.

Example 4

Synthesis of Methacrylated (MMA) Phosphinated Ethylpolyphenylene Oxide of Formula (IIIc-M)

1.0 g of the oligomers of formula (IIc) synthesized in Example 3 and 0.01 g (2 mol % of methacrylic anhydride) DMAP were dissolved in a dimethylacetamide (DMAc) solvent of 15 mL and were reacted under an argon atmosphere at room temperature for 1 hour. Then, 0.665 g methacrylic anhydride was added and reacted at room temperature for 3 hours and subsequently at a temperature of 45° C. for 24 hours. After the reaction was terminated, the product was precipitated using a saturated $NaHCO_3$ solution (to remove the acid) and was rinsed with water several times. After suction filtration, the filtered cake was dried in a vacuum oven at a temperature of 50° C. The yield was about 85%. The Fourier transform infrared spectroscopy (FTIR) analysis result shows that the characteristic peak of —O—C=O— is at 1735 $cm^{-1}$, and the characteristic peak of —C=C— is at 1649 $cm^{-1}$. The produced methacrylated (MMA) phosphinated ethylpolyphenylene oxide is represented by the following formula:

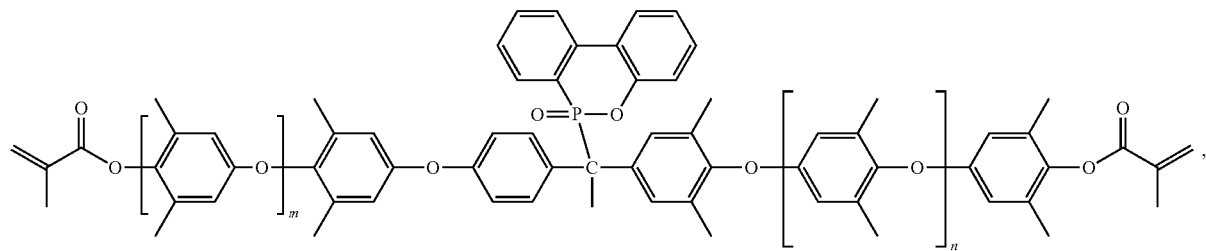

(IIIc-M)

wherein m or n each independently denotes an integer from 0 to 30, preferably an integer from 0 to 20.

The characteristic peaks of 2.0, 5.9, and 6.3 ppm shown in the $^1$H NMR spectrum of the oligomer of formula (IIIc-M) correspond to an acrylate group. The above result confirms that the resulting molecular structure is correct.

Example 5

Synthesis of Allylated Phosphinated Ethyl Polyphenylene Oxide of Formula (IIIc-A)

1.0 g of the oligomers of formula (IIc) synthesized in Example 3, 0.23 g allyl bromine, and 0.1 g $K_2CO_3$ were dissolved in a DMAc solvent of 15 mL and were reacted under a nitrogen atmosphere at an elevated temperature of 65° C. for 24 hours. After the reaction was terminated, the temperature was cooled to room temperature. The salts were filtered out to collecting the filtrate. The filtrate was added to an iced saturated brine. After suction filtration, the filtered cake was dried in a vacuum oven at a temperature of 60° C. to produce a slightly sticky khaki solid product. The yield was about 70%. The FTIR result shows a characteristic peak of an allyl group at 915 cm$^{-1}$. The produced allylated phosphinated ethyl polyphenylene oxide is represented by the following formula:

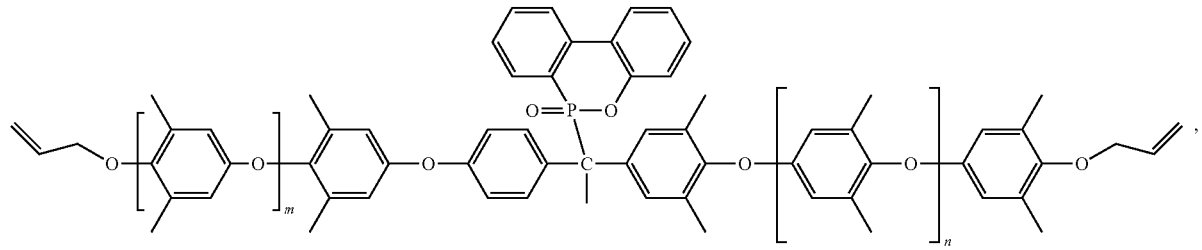

(IIIc-A)

wherein m or n each independently denotes an integer from 0 to 30, preferably an integer from 0 to 20.

The characteristic peaks of 4.8, 5.3, and 6.1 ppm shown in the $^1$H NMR spectrum of the oligomer of formula (IIIc-A) correspond to an allyl group. The above result confirms that the resulting molecular structure is correct.

Example 6

Synthesis of Vinylbenzylated Phosphinated Ethyl Polyphenylene Oxide of Formula (IIIc-VB)

1.0 g of the oligomers of formula (IIc) synthesized in Example 3, 1.4 g 4-chloromethylstyrene, and 0.1 g $K_2CO_3$ were dissolved in a DMAc solvent of 15 mL and were reacted under a nitrogen atmosphere at a temperature of 120° C. for 12 hours. After the reaction was terminated, a khaki powder was precipitated by using ethanol and was rinsed several times. After suction filtration, the filtered cake was dried in a vacuum oven at a temperature of 80° C. The yield was about 88%. The produced vinylbenzylated phosphinated ethyl polyphenylene oxide is represented by the following formula:

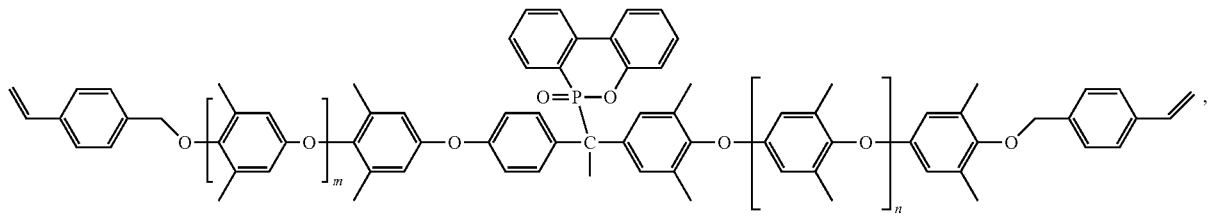

(IIIc-VB)

wherein m or n each independently denotes an integer from 0 to 30, preferably an integer from 0 to 20.

Figure 3:
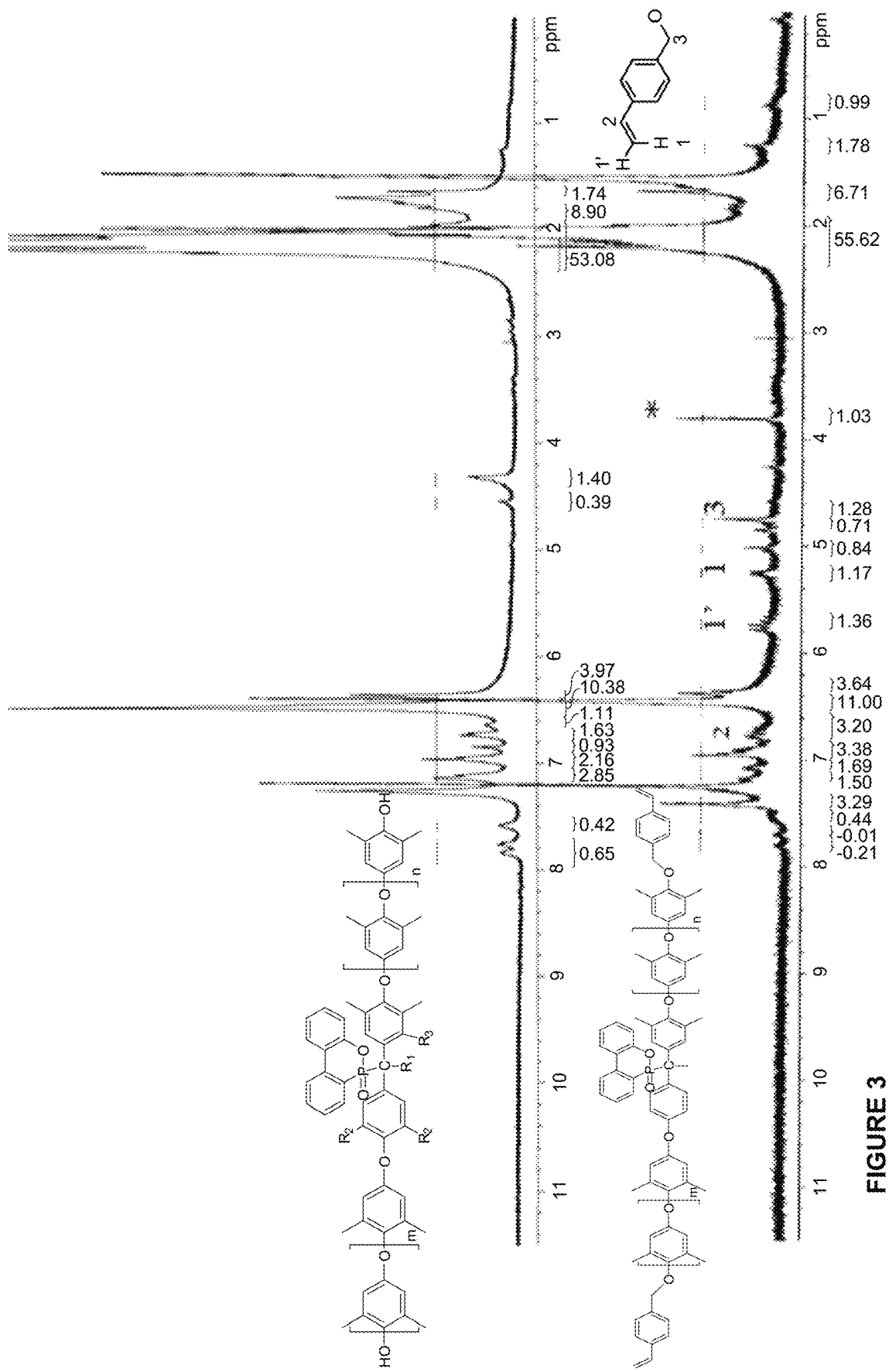
FIG. 3 shows an overlapping $^1$H-NMR spectrum of oligomers of formulae (IIc) and (IIIc-VB).

FIG. 3 shows a $^1$H NMR spectrum of the oligomers of formulae (IIc) and (IIIc-VB). It can be found in FIG. 3 that the peak(s) related to an OH functional group of the oligomer of formula (IIc) (4.3-4.6 ppm) disappeared, and the characteristic peaks of a 4-chloromethylstyrene structure of the oligomer of formula (IIIc-VB) are present at 5.2 (=CH, marked as 1), 5.8 (=CH$_1$, marked as 1'), and 4.8 (CH$_2$, marked as 3).

Example 7

Synthesis and Characterization of a Thermoset Produced from Methacrylated (MMA) Phosphinated Ethylpolyphenylene Oxide of Formula (IIIc-M)

Figure 4:
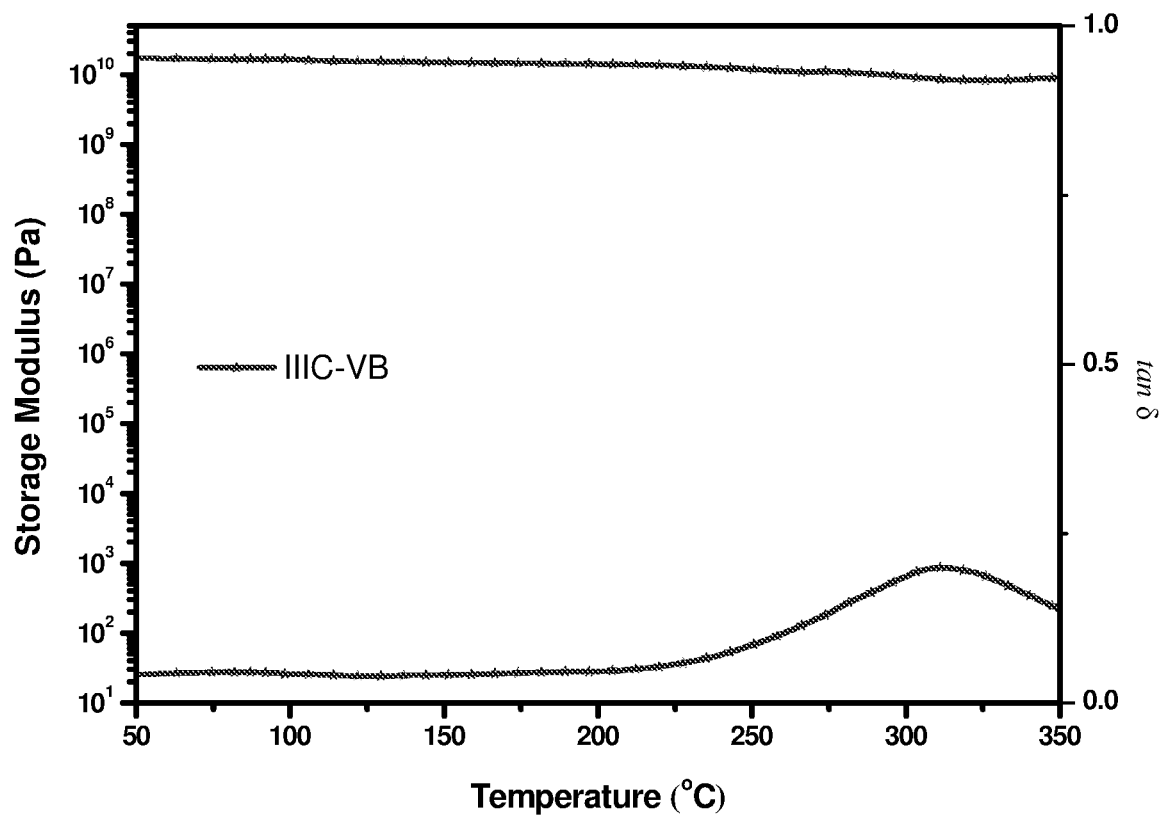
FIG. 4 shows a DMA profile of a thermoset produced by curing an oligomer of formula (IIIc-VB) with an initiator of t-butyl cumyl peroxide (TBCP).

1.0 g of the oligomers of formula (IIIc-M) synthesized in Example 4 were dissolved in an NMP solvent to produce a solution having 30 wt % solid content. After complete dissolution, a free-radical reaction was conducted by adding 1 wt % t-butyl cumyl peroxide (TBCP) to produce a film. The film was dried in a circulation oven at a temperature of 110° C. for 12 hours to remove most of the solvent. Then, the temperature was elevated to 180° C., 200° C., and 220° C. and maintained at each step temperature for 2 hours. Finally, a phenol film was produced by dipping the glass substrate in water and was then analyzed to obtain its thermal properties. The dynamic mechanical analysis (DMA) result of the produced thermoset is shown in FIG. 4, where the Tg of the produced thermoset is determined to be 277° C. Regarding the dielectric constant (Dk), the refractive index (n) was measured to be 1.55 by ellipsometry using an incident wavelength of 633 nm According to the equation "Dk=1.1 n$^2$," the dielectric constant of the thermoset produced from the oligomers of formula (IIIc-M) can be computed as 2.64 (U), which reveals that the produced thermoset has a relatively low dielectric constant.

Example 8

Synthesis and Characterization of the Thermoset Produced from Allylated Phosphinated Ethylpolyphenylene Oxide of Formula (IIIc-A)

1.0 g of the oligomers of formula (IIIc-A) synthesized in Example 5 were dissolved in an NMP solvent to produce a solution having 30 wt % solid content. After complete dissolution, a free-radical reaction was conducted by adding 1 wt % t-butyl cumyl peroxide (TBCP) to produce a film. The film was dried in a circulation oven at a temperature of 110° C. for 12 hours to remove most of the solvent. Then, the temperature was elevated to 180° C., 200° C., and 220° C. and maintained at each step temperature for 2 hours. Finally, a phenol film was produced by dipping the glass substrate in water and was then analyzed to obtain its thermal properties. The dynamic mechanical analysis (DMA) result shows that the Tg of the produced thermoset is 294° C. Regarding the dielectric constant (Dk), the refractive index (n) was measured to be 1.59 by ellipsometry using an incident wavelength of 633 nm According to the equation "Dk=1.1 n$^2$," the dielectric constant of the thermoset produced from the oligomers of formula (IIIc-A) can be computed as 2.78 (U).

Example 9

Synthesis and Characterization of the Thermoset Produced from Vinylbenzylated Phosphinated Ethyl Polyphenylene Oxide of Formula (IIIc-VB)

Figure 5:
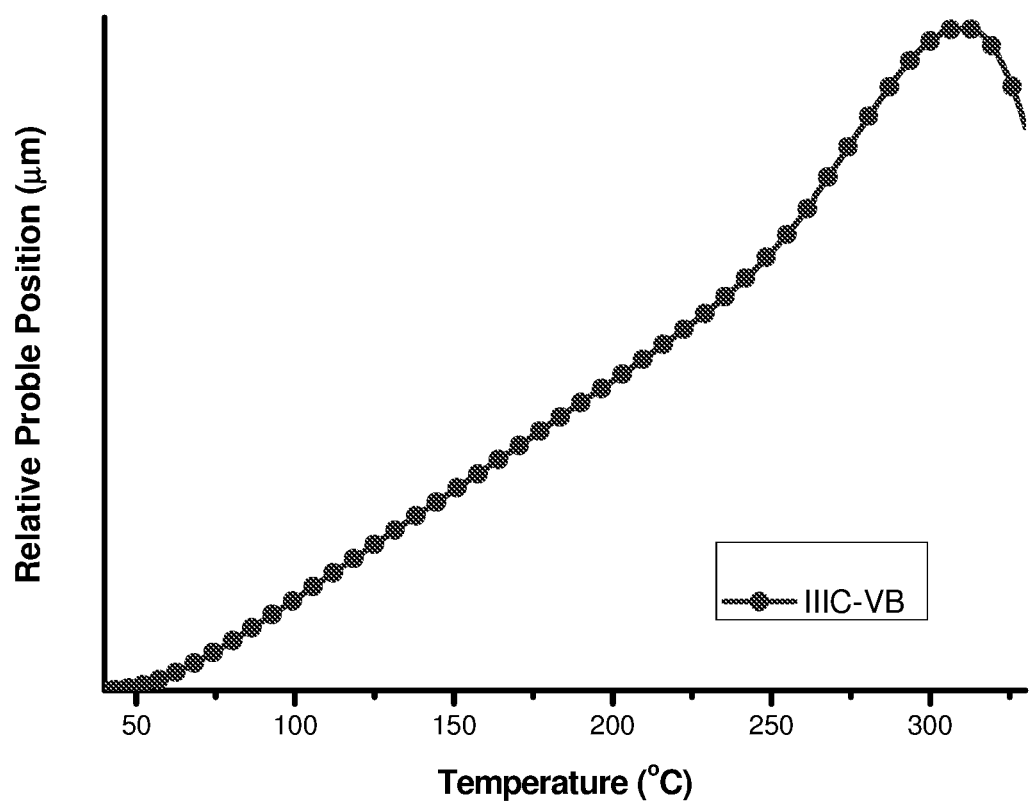
FIG. 5 shows a TMA profile of a thermoset produced by curing an oligomer of formula (IIIc-VB) with an initiator of t-butyl cumyl peroxide (TBCP).
Figure 6:
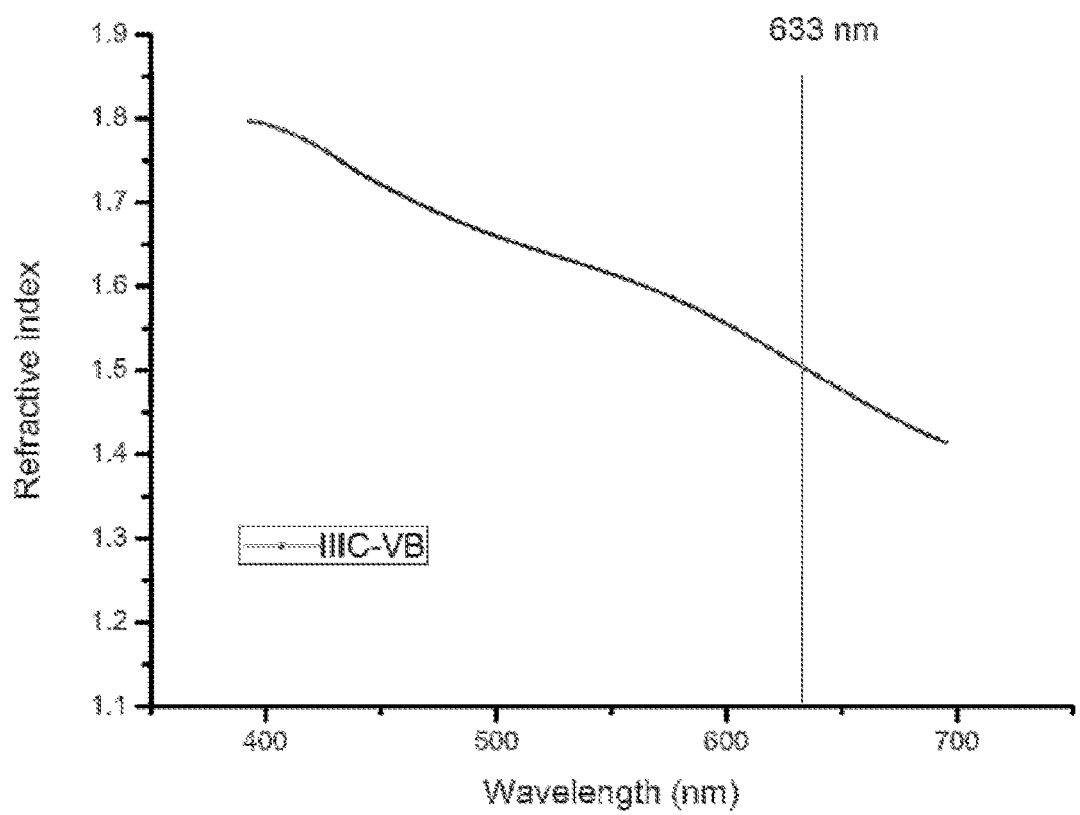
FIG. 6 shows an ellipsometry measurement result of a thermoset produced by curing an oligomer of formula (IIIc-VB) with an initiator of t-butyl cumyl peroxide (TBCP).

1.0 g of the oligomers of formula (IIIc-VB) synthesized in Example 6 were dissolved in an NMP solvent to produce a solution having 30 wt % solid content. After complete dissolution, a free-radical reaction was conducted by adding 1 wt % t-butyl cumyl peroxide (TBCP) to produce a film. The film was dried in a circulation oven at a temperature of 110° C. for 12 hours to remove most of the solvent. Then, the temperature was elevated to 180° C., 200° C., and 220° C. and maintained at each step temperature for 2 hours. Finally, a phenol film was produced by dipping the glass substrate in water and was then analyzed to obtain its thermal properties. The dynamic mechanical analysis (DMA) result of the produced thermoset is shown in FIG. 4, where the Tg of the produced thermoset was determined to be 314° C. In addition, the thermomechanical analysis (TMA) shown in FIG. 5 reveals that the Tg of the produced thermoset was measured to be 302° C. The above results confirm that the thermoset of the present invention exhibits superior thermal properties. Regarding the dielectric constant (Dk), the refractive index (n) was measured to be 1.50 by ellipsometry using an incident wavelength of 633 nm According to the equation "Dk=1.1 n$^2$," the dielectric constant of the thermoset produced from the oligomers of formula (IIIc-VB) can be computed as 2.48 (U), which reveals that the produced thermoset has a relatively low dielectric constant, as shown in FIG. 6.

What is claimed is:
1. A phosphinated poly(2,6-dimethyl phenylene oxide) oligomer of formula (2):

(2)

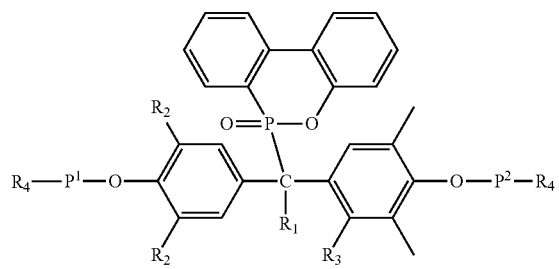

wherein each group has the following meaning:
P¹ denotes

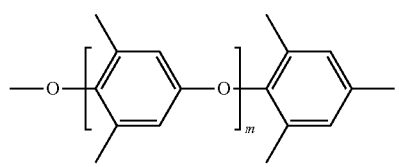

P² denotes

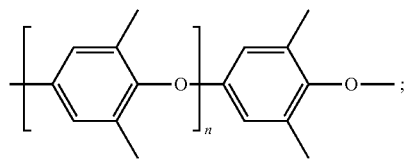

$R_1$, $R_3$ each independently denotes H or a straight chain or branched chain alkyl having 1 to 6 C-atoms;

$R_2$ each independently denotes H, or a straight chain or branched chain alkyl having 1 to 6 C-atoms, and at least one $R_2$ is H;

$R_4$ denotes H, alkenyl or aryl having 1 to 10 C-atoms and comprising 0 to 3 oxygen atoms, or the combination thereof; and m, n each independently denotes an integer from 0 to 30.

2. The oligomer according to claim 1, wherein at least the oligomer of formula (2) comprises a phosphinated poly(2,6-dimethyl phenylene oxide) bisphenol oligomer of formula (3):

(3)

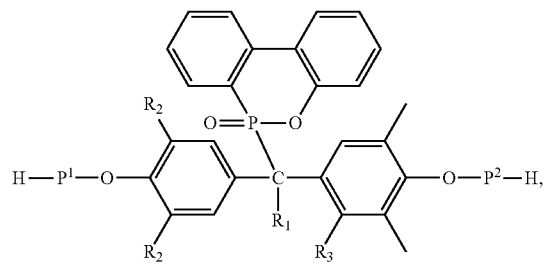

wherein P¹, P², $R_1$, $R_2$, $R_3$, m, and n are as defined in claim 1.

3. The oligomer according to claim 2, wherein at least the oligomer of formula (3) comprises a phosphinated poly(2,6-dimethyl phenylene oxide) bisphenol oligomer of formula (IIc):

(IIc)

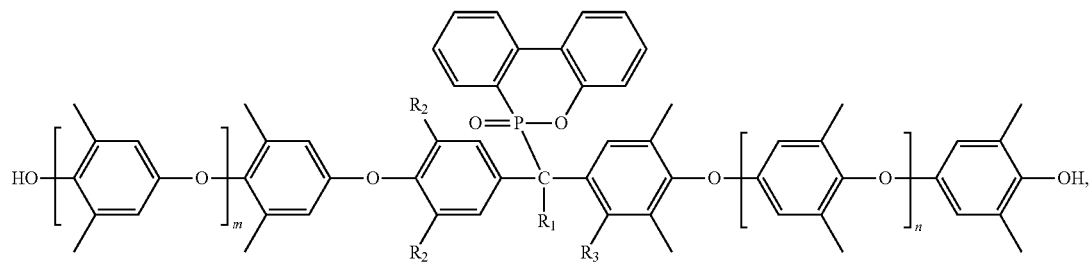

wherein $R_1$, and $R_3$ are each independently H, or a straight chain or branched chain alkyl having 1 to 6 C-atoms;

$R_2$ is each independently H, or a straight chain or branched chain alkyl having 1 to 6 C-atoms, and at least one $R_2$ is H; and m, and n are each independently an integer from 0 to 30.

4. The oligomer according to claim 1, wherein $R_4$ is alkenyl or aryl having 1 to 10 C-atoms and comprising 0 to 3 oxygen atoms, or the combination thereof.

5. The oligomer according to claim 1, wherein $R_4$ denotes

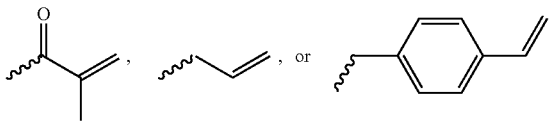

6. The oligomer according to claim 1, wherein at least the oligomer of formula (2) comprises an unsaturated group-containing phosphinated poly(2,6-dimethyl phenylene oxide) oligomer of formula (IIIc),

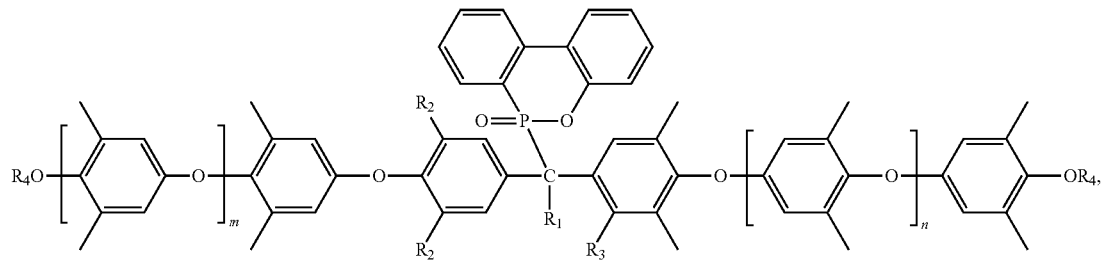

(IIIc)

wherein $R_1$, and $R_3$ are each independently H, or a straight chain or branched chain alkyl having 1 to 6 C-atoms;

$R_2$ each independently is H, or a straight chain or branched chain alkyl having 1 to 6 C-atoms, and at least one $R_2$ is H;

m, and n are each independently an integer from 0 to 30; and $R_4$ denotes

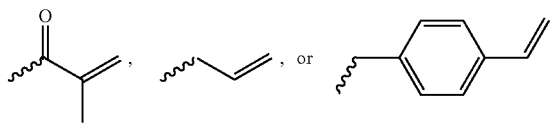

7. The oligomer according to claim 1, wherein $R_1$, and $R_3$ each independently denote H, $CH_3$, or $C_2H_5$, one $R_2$ denotes H, the other $R_2$ denotes $CH_3$ or $C_2H_5$, and m and n each independently denote an integer from 0 to 20.

8. The oligomer according to claim 1, wherein at least the oligomer of formula (2) comprises an unsaturated group-containing phosphinated poly(2,6-dimethyl phenylene oxide) oligomer of formula (IIIc-M), (IIIc-A) or (IIIc-VB):

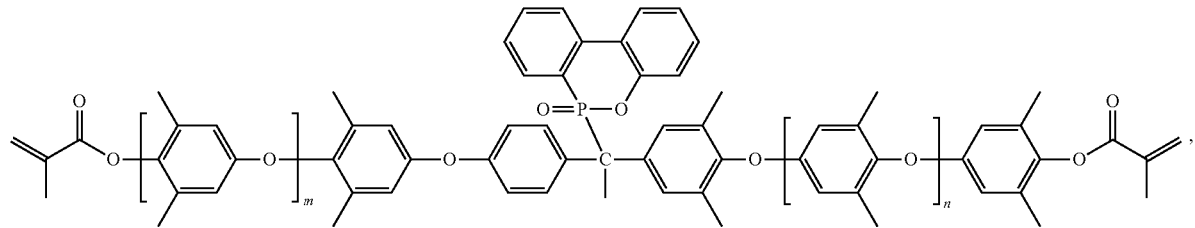

(IIIc-M)

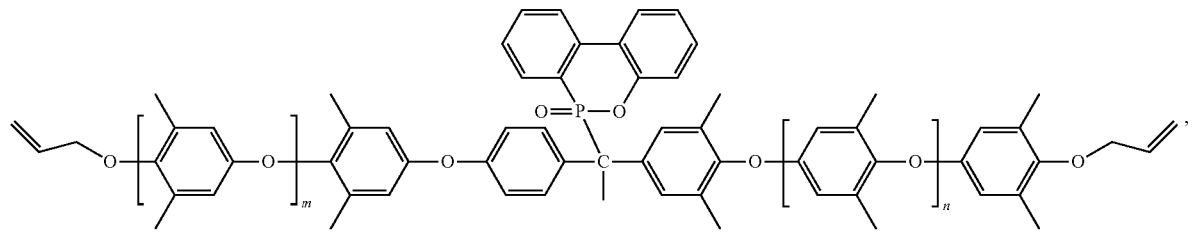

(IIIc-A)

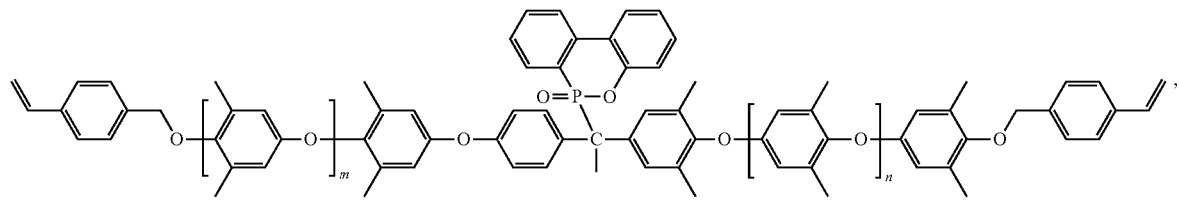

(IIIc-VB)

wherein m and n are each independently an integer from 0 to 30.

9. A process for producing the oligomer of formula (3) set forth in claim 2, comprising a reaction of compound of formula (I):

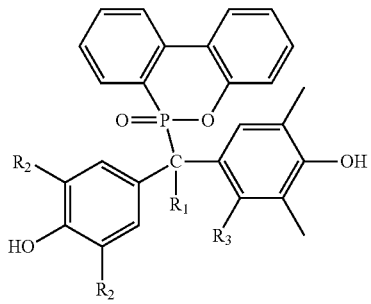

with poly(2,6-dimethyl phenylene oxide) under the catalysis of CuCl and an amine compound to produce a phosphinated poly(2,6-dimethyl phenylene oxide) bisphenol oligomer of formula (3), wherein $R_1$, and $R_3$ are each independently H, or a straight chain or branched chain alkyl having 1 to 6 C-atoms; $R_2$ is each independently H, or a straight chain or branched chain alkyl having 1 to 6 C-atoms, and at least one $R_2$ is H.

10. The process according to claim 9, wherein the amine compound comprises dibutylamine or 4-dimethylaminopyridine.

11. A process for preparing the oligomer of formula (3) set forth in claim 2, comprising conducting a redistribution reaction for a compound of formula (I):

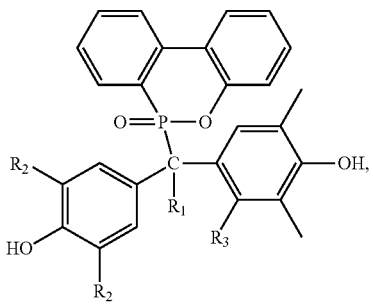

wherein $R_1$, and $R_3$ are each independently H, or a straight chain or branched chain alkyl having 1 to 6 C-atoms; $R_2$ is each independently H, or a straight chain or branched chain alkyl having 1 to 6 C-atoms, and at least one $R_2$ is H;

and a poly(2,6-dimethyl phenylene oxide) oligomer of formula (5):

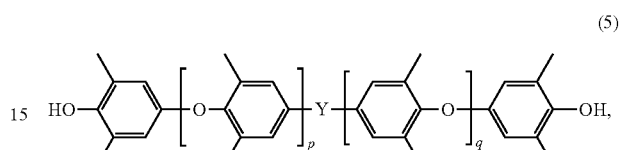

wherein
Y denotes

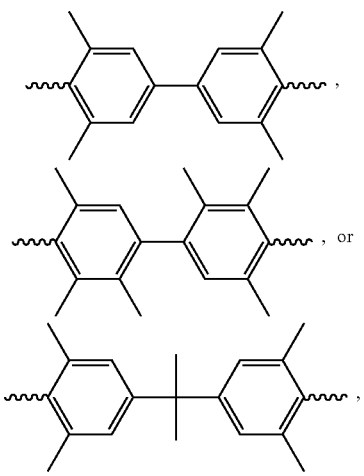

and p, q each independently denotes an integer from 0 to 50;

under the catalysis of a benzoyl peroxide to produce a phosphinated poly(2,6-dimethyl phenylene oxide) bisphenol oligomer of formula (3).

12. The process according to claim 11, wherein the produced phosphinated poly(2,6-dimethyl phenylene oxide) bisphenol oligomer of formula (3) comprises at least an oligomer of formula (IIc)

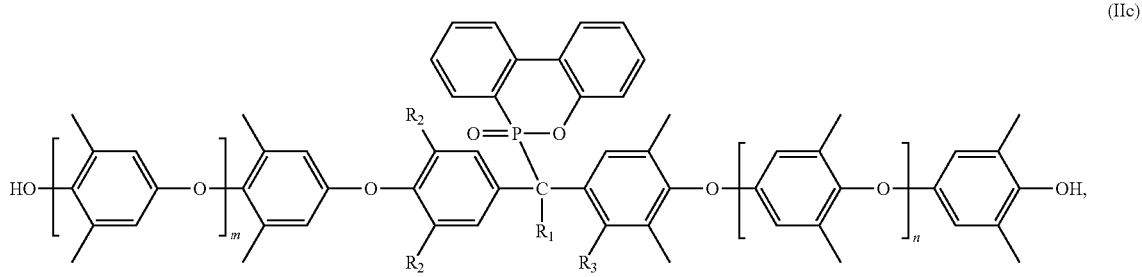

wherein R₁, and R₃ are each independently H, or a straight chain or branched chain alkyl having 1 to 6 C-atoms; R₂ is each independently H, or a straight chain or branched chain alkyl having 1 to 6 C-atoms, and at least one R₂ is H; and m, and n are each independently an integer from 0 to 30.

13. A process for producing the compound of formula (2) set forth in claim 1, comprising reacting a phosphinated poly(2,6-dimethyl phenylene oxide) bisphenol oligomer of formula (3)

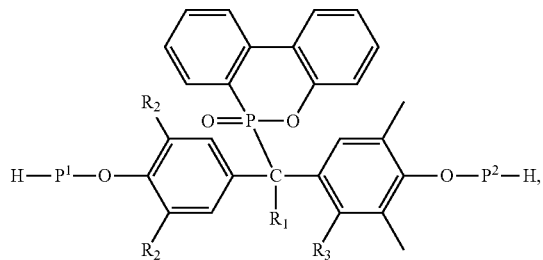

(3)

wherein:
P¹ is

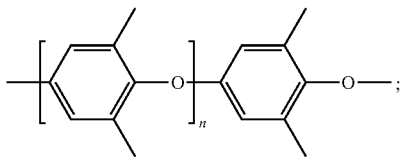

P² is

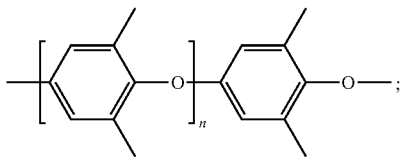

R₁, and R₃ are each independently H, or a straight chain or branched chain alkyl having 1 to 6 C-atoms;

R₂ each independently is H, or a straight chain or branched chain alkyl having 1 to 6 C-atoms, and at least one R₂ is H; and m, and n are each independently an integer from 0 to 30, with methacrylic anhydride, allyl bromine, or 4-chloromethylstyrene under the catalysis of a alkali catalyst to produce an unsaturated group-containing phosphinated poly(2,6-dimethyl phenylene oxide) oligomer of formula (2).

14. The process according to claim 13, wherein the phosphinated poly(2,6-dimethyl phenylene oxide) bisphenol oligomer of formula (3) comprises an oligomer of formula (IIc)

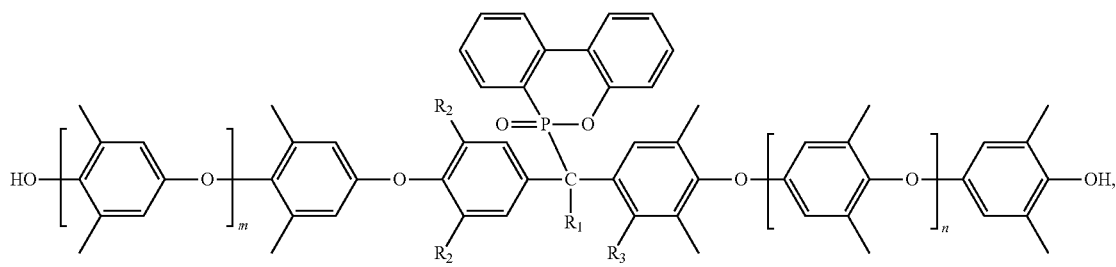

(IIc)

wherein R₁, and R₃ are each independently H, or a straight chain or branched chain alkyl having 1 to 6 C-atoms; R₂ is each independently H, or a straight chain or branched chain alkyl having 1 to 6 C-atoms, and at least one R₂ is H; and m, and n are each independently an integer from 0 to 30.

15. The process according to claim 13, wherein the alkali catalyst is selected from the group consisting of potassium carbonate (K₂CO₃), sodium carbonate (Na₂CO₃), potassium hydroxide (KOH), sodium hydroxide (NaOH), sodium bicarbonate (NaHCO₃), and the combination thereof.

16. The process according to claim 13, wherein the produced unsaturated group-containing phosphinated poly(2,6-dimethyl phenylene oxide) oligomer of formula (4) comprises an oligomer of formula (IIIc), (IIIc)

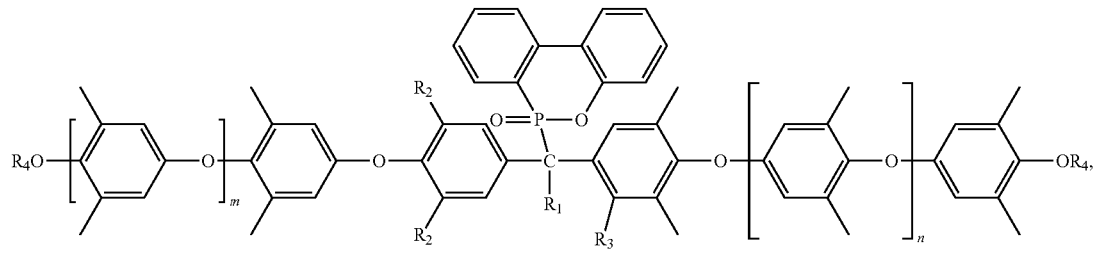

wherein:
$R_1$, and $R_3$ are each independently H, or a straight chain or branched chain alkyl having 1 to 6 C-atoms;
$R_2$ is each independently H, or a straight chain or branched chain alkyl having 1 to 6 C-atoms, and at least one $R_2$ is H;
m, and n are each independently an integer from 0 to 30; and
$R_4$ is

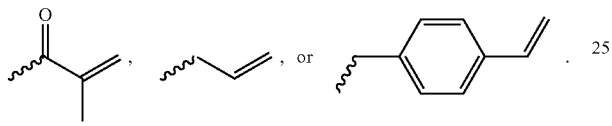

17. The process according to claim 16, wherein the produced unsaturated group-containing phosphinated poly (2,6-dimethyl phenylene oxide) oligomer of formula (4) comprises an oligomer of formula (IIIc-M), (IIIc-A), or (IIIc-VB), (IIIc-M)

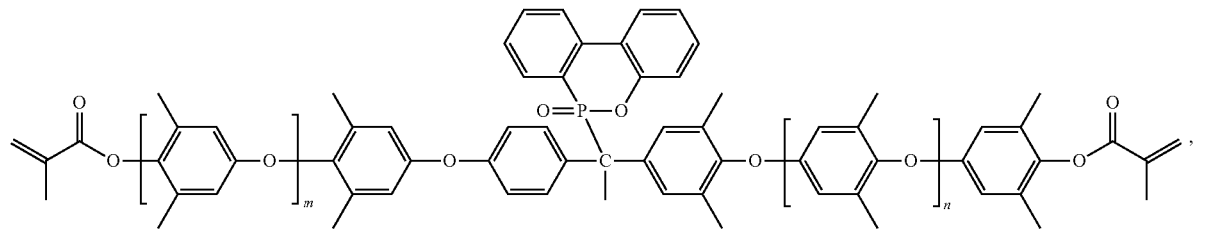

(IIIc-A)

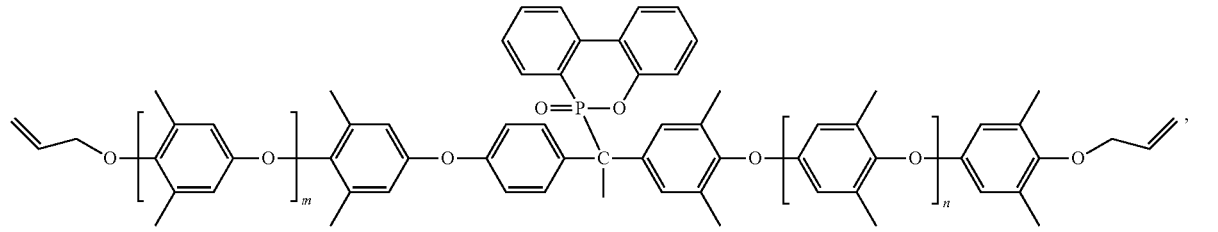

(IIIc-VB)

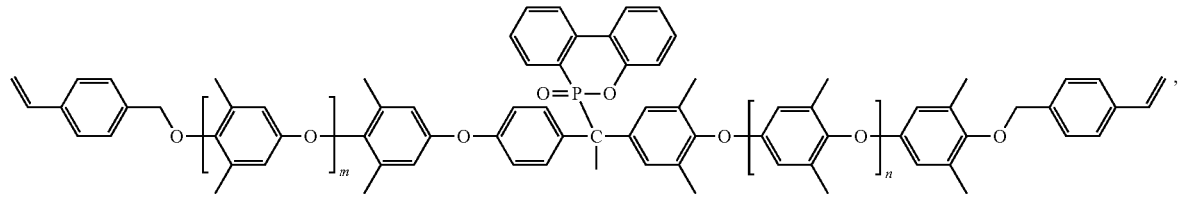

wherein m, and n are each independently an integer from 0 to 30.

18. A thermoset produced from curing the oligomer of formula (2) set forth in claim 1 with a radical initiator.

19. The thermoset according to claim 18, wherein the oligomer of formula (2) comprises an oligomer of formula (IIIc-M), (IIIc-A), or (IIIc-VB),

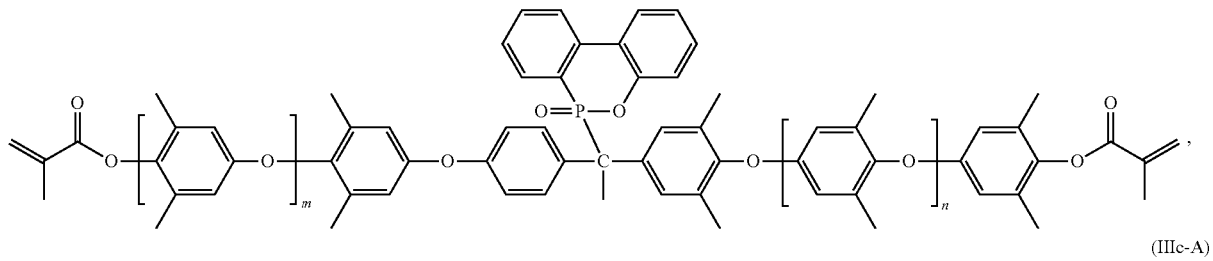

(IIIc-M)

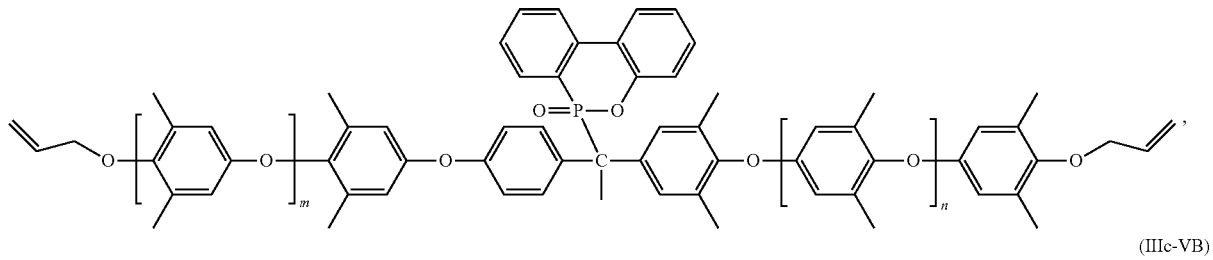

(IIIc-A)

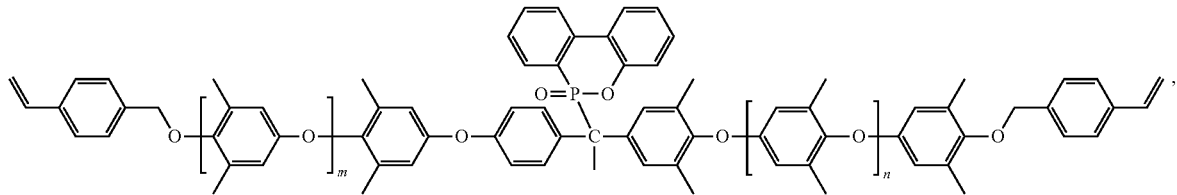

(IIIc-VB)

wherein m, and n are each independently an integer from 0 to 30.

20. The thermoset according to claim 18, wherein the radical initiator comprises a peroxide.

21. The thermoset according to claim 18, therein the radical initiator comprises t-butyl cumyl peroxide (TBCP).

* * * * *